US009603919B2

(12) United States Patent
Hasegawa et al.

(10) Patent No.: US 9,603,919 B2

(45) Date of Patent: Mar. 28, 2017

(54) METHOD FOR PROPHYLAXIS OF INFLUENZA USING VACCINE FOR INTRANASAL ADMINISTRATION

(75) Inventors: Hideki Hasegawa, Tokyo (JP); Sadao Manabe, Kanonji (JP); Takeshi Tanimoto, Kanonji (JP); Takashi Miyazaki, Nakaniikawa-gun (JP); Taizou Kamishita, Takatsuki (JP)

(73) Assignees: JAPAN AS REPRESENTED BY THE DIRECTOR-GENERAL OF NATIONAL INSTITUTE OF INFECTIOUS DISEASES, Tokyo (JP); THE RESEARCH FOUNDATION FOR MICROBIAL DISEASES OF OSAKA UNIVERSITY, Suita (JP); TOKO YAKUHIN KOGYO KABUSHIKI KAISHA, Osaka (JP)

(*) Notice: Subject to any disclaimer, the term of this patent is extended or adjusted under 35 U.S.C. 154(b) by 0 days.

(21) Appl. No.: 13/262,515

(22) PCT Filed: Mar. 31, 2010

(86) PCT No.: PCT/JP2010/056274

§ 371 (c)(1), (2), (4) Date: Dec. 21, 2011

(87) PCT Pub. No.: WO2010/114169

PCT Pub. Date: Oct. 7, 2010

(65) Prior Publication Data

US 2012/0082697 A1 Apr. 5, 2012

Related U.S. Application Data

(60) Provisional application No. 61/165,098, filed on Mar. 31, 2009.

(51) Int. Cl.

| | |
|---|---|
| ***A61K 39/145*** | (2006.01) |
| ***A61K 39/12*** | (2006.01) |
| ***A61K 39/39*** | (2006.01) |
| ***A61K 39/00*** | (2006.01) |
| ***A61K 38/00*** | (2006.01) |
| ***C07K 14/005*** | (2006.01) |
| ***C12N 7/00*** | (2006.01) |

(52) U.S. Cl.

CPC ............ *A61K 39/145* (2013.01); *A61K 39/12* (2013.01); *A61K 39/39* (2013.01); *A61K 2039/525* (2013.01); *A61K 2039/5254* (2013.01); *A61K 2039/543* (2013.01); *A61K 2039/55555* (2013.01); *A61K 2039/55561* (2013.01); *A61K 2039/58* (2013.01); *A61K 2039/6093* (2013.01); *C12N 2760/16134* (2013.01)

(58) Field of Classification Search

CPC A61K 2300/00; A61K 38/00; A61K 31/7115; A61K 39/12; A61K 48/0075; A61K 39/39; A61K 9/145; A61K 2039/5254; A61K 2039/525; A61K 31/712; A61K 31/7125; A61K 39/145; A61K 2039/53; A61K 2039/54; A61K 2039/543

See application file for complete search history.

(56) References Cited

U.S. PATENT DOCUMENTS

| | | | | | |
|---|---|---|---|---|---|
| 5,026,543 | A * | 6/1991 | Rijke | 424/78.31 | |
| 5,158,761 | A | 10/1992 | Kamishita et al. | | |
| 5,215,739 | A | 6/1993 | Kamishita et al. | | |
| 5,679,356 | A * | 10/1997 | Bonnem | A61K 39/145 | 424/209.1 |
| 2003/0099659 | A1* | 5/2003 | Gizurarson | A61K 9/0043 | 424/184.1 |
| 2004/0228921 | A1* | 11/2004 | Chowdhury | A61K 9/0048 | 424/488 |
| 2005/0281843 | A1 | 12/2005 | Singh et al. | | |
| 2007/0048821 | A1* | 3/2007 | Minke | A61K 39/145 | 435/69.1 |
| 2007/0166239 | A1 | 7/2007 | Lin et al. | | |
| 2007/0219149 | A1 | 9/2007 | Hasegawa et al. | | |
| 2007/0224219 | A1 | 9/2007 | Carter et al. | | |
| 2009/0017067 | A1 | 1/2009 | Diehl et al. | | |
| 2009/0104228 | A1* | 4/2009 | Rudenko | A61K 39/145 | 424/206.1 |

(Continued)

FOREIGN PATENT DOCUMENTS

| | | | |
|---|---|---|---|
| EP | 0303516 | A2 * | 2/1989 |
| EP | 1 666 059 | A1 | 6/2006 |

(Continued)

OTHER PUBLICATIONS

Lin et al. Baculovirus-derived hemagglutinin vaccine protects chickens from lethal homologous virus H5N1 challenge. The Journal of Veterinary Medical Science, Nov. 2008;70(11):1147-52.*

Asahi-Ozaki et al. Intranasal administration of adjuvant-combined recombinant influenza virus HA vaccine protects mice from the lethal H5N1 virus infection. Microbes and Infection, 2006, vol. 8, 2706-2714.*

Ichinohe et al. Cross-protection against H5N1 influenza virus infection is afforded by intranasal inoculation with seasonal trivalent inactivated influenza vaccine. The Journal of Infectious Disease, 2007, vol. 196, 1313-1320.*

(Continued)

*Primary Examiner* — Rachel B Gill

(74) *Attorney, Agent, or Firm* — Leydig, Voit & Mayer, Ltd.

(57) ABSTRACT

The present invention provides a vaccine composition for transnasal mucous membrane administration, which contains an influenza virus antigen, polyriboinosinic polyribocytidylic acid (poly (I:C)) or a derivative thereof and a carboxyvinyl polymer. The present invention also provides a prophylactic method of influenza, including a step of administering the vaccine composition at least once to the nasal mucosa of a subject in need thereof.

27 Claims, 6 Drawing Sheets

(56) References Cited

U.S. PATENT DOCUMENTS

| | | | | |
|---|---|---|---|---|
| 2009/0186048 | A1* | 7/2009 | Aagaard et al. | 424/190.1 |
| 2009/0311334 | A1 | 12/2009 | Lin et al. | |
| 2010/0074915 | A1* | 3/2010 | Haynes | 424/186.1 |
| 2011/0223198 | A1 | 9/2011 | Carter et al. | |
| 2015/0307884 | A1 | 10/2015 | Nakano et al. | |
| 2016/0015800 | A1* | 1/2016 | Hasegawa | A61K 9/0043 424/209.1 |

FOREIGN PATENT DOCUMENTS

| | | | | |
|---|---|---|---|---|
| JP | 03-038529 | A | | 2/1991 |
| WO | WO 94/20070 | A1 | | 9/1994 |
| WO | WO 00/50078 | A1 | | 8/2000 |
| WO | WO 01/17556 | A1 | * | 3/2001 |
| WO | WO 2005/014038 | A1 | | 2/2005 |
| WO | WO 2007/067517 | A2 | | 6/2007 |
| WO | WO 2007/081288 | A1 | | 7/2007 |
| WO | WO 2008/157659 | A1 | | 12/2008 |
| WO | WO 2009/118523 | A1 | | 10/2009 |

OTHER PUBLICATIONS

Oka et al. Influenza vaccine: enhancement of immune response by application of carboxy-vinylpolymer, Vaccine, 1990, vol. 8, 573-576.*

Ainai A, et. al. Characterization of neutralizing antibodies in adults after intranasal vaccination with an inactivated influenza vaccine. J Med Virol. Feb. 2012;84(2):336-44.*

"Influenza Reagent. Influenza virus infectious NIBRG-14; Instructions for use." National Institute for Biological Standards and Control (NIBSC). Ver.2.0. Mar. 31, 2008.*

CDC Fact Sheet: Influenza—"Vaccine Effectiveness: How Well Does the Flu Vaccine Work?" Centers for Disease Control and Prevention. Jan. 31, 2014.*

Lubrizol. "Polymers for Pharmaceutical Applications." Pharmaceutical Bulletin 1. May 31, 2011. https://www.lubrizol.com/Life-Science/Documents/Pharmaceutical/Bulletins/Bulletin-01---Polymers-for-Pharmaceutical-Applications.pdf.*

Reagan-Shaw S, Nihal M, Ahmad N. Dose translation from animal to human studies revisited. FASEB J. Mar. 2008;22(3):659-61. Epub Oct. 17, 2007.*

World Health Organization (WHO) Expert Committee on Biological Standardization, Proposed Guidelines: Regulatory Preparedness for Human Pandemic Influenza Vaccines, Geneva Oct. 8-12, 2007.*

Hafner AM, Corthésy B, Merkle HP. Particulate formulations for the delivery of poly(I:C) as vaccine adjuvant. Adv Drug Deliv Rev. Oct. 2013;65(10):1386-99. Epub Jun. 7, 2013.*

Jin B, Sun T, Yu XH, Liu CQ, Yang YX, Lu P, Fu SF, Qiu HB, Yeo AE. Immunomodulatory effects of dsRNA and its potential as vaccine adjuvant. J Biomed Biotechnol. 2010;2010:690438. doi: 10.1155/2010/690438. Epub Jul. 5, 2010.*

Stahl-Hennig C, et. al. Synthetic double-stranded RNAs are adjuvants for the induction of T helper 1 and humoral immune responses to human papillomavirus in rhesus macaques. PLoS Pathog. Apr. 2009;5(4):e1000373. Epub Apr. 10, 2009.*

Absher M, Stinebring WR. Toxic properties of a synthetic double-stranded rna: endotoxin-like properties of poly I.Poly C, an interferon stimulator. Nature, vol. 223, No. 5207, pp. 715-717, 1969.*

Robinson RA, DeVita VT, Levy HB, Baron S, Hubbard SP, Levine AS. A phase I-II trial of multiple-dose polyriboinosic-polyribocytidylic acid in patieonts with leukemia or solid tumors, Journal of the National Cancer Institute, vol. 57, No. 3, pp. 599-602, 1976.*

Lubrizol. Carbopol® Polymers for Controlled Release Matrix Tablets: Frequently Asked Questions. © 2008. http://images.alfresco.advanstar.com/alfresco_images/pharma/2014/08/21/fc7f389b-ffd9-4b15-838d-0cf07941cadd/article-595018.pdf.*

Asahi-Ozaki et al., "Intranasal administration of adjuvant-combined recombinant influenza virus HA vaccine protects mice from the lethal H5N1 virus infection," *Microbes and Infection*, 8(12-13): 2706-2714 (2006).

Coucke et al., "Spray-dried powders of starch and crosslinked poly(acrylic acid) as carriers for nasal delivery of inactivated influenza vaccine," *Vaccine*, 27(8): 1279-1286 (2009).

Ichinohe et al., "Innate sensors of influenza virus: clues to developing better intranasal vaccines," *Expert Rev. Vaccines*, 7(9): 1435-1445 (2008).

Ichinohe et al., "Cross-Protection against H5N1 influenza virus infection is afforded by intranasal inoculation with seasonal trivalent inactivated influenza vaccine," *The Journal of Infectious Diseases*, 196(9): 1313-1320 (2007).

Ichinohe et al., "Intranasal immunization with H5N1 vaccine plus Poly I:Poly $C_{12}U$, a Toll-like receptor agonist, protects mice against homologous and heterologous virus challenge," *Microbes and Infection*, 9(11): 1333-1340 (2007).

Ichinohe et al., "Polyl:poly$C_{12}U$ adjuvant-combined intranasal vaccine protects mice against highly pathogenic H5N1 influenza virus variants," *Vaccine*, 27(45): 6276-6279 (2009).

Oka et al., "Influenza vaccine: enhancement of immune response by application of carboxy-vinylpolymer," *Vaccine*, 8(6): 573-576 (1990).

O'Hagan et al., "MF59 Is a Safe and Potent Vaccine Adjuvant for Flu Vaccines in Humans: What Did We Learn During Its Development?" *Clinical Pharmacology and Therapeutics*, 82(6): 740-744 (Dec. 2007).

Asahi-Ozaki et al., *Microbes and Infection*, 8(12-13): 2706-2714 (2006).

Coucke et al., *Vaccine*, 27(8): 1279-1286 (2009).

Ichinohe et al., *Expert Rev. Vaccines*, 7(9): 1435-1445 (2008).

Ichinohe et al., *The Journal of Infectious Diseases*, 196(9): 1313-1320 (2007).

Ichinohe et al., *Microbes and Infection*, 9(11): 1333-1340 (2007).

Ichinohe et al., *Vaccine*, 27(45): 6276-6279 (2009).

Oka et al., *Vaccine*, 8(6): 573-576 (1990).

European Patent Office; International Search Report in International Patent Application No. PCT/JP2010/056274 (Jul. 6, 2010).

European Patent Office; Written Opinion in International Patent Application No. PCT/JP2010/056274 (Jul. 6, 2010).

Ichinobe et al., "Synthetic Double-Stranded RNA Poly(I:C) Combined with Mucosal Vaccine Protects against Influenza Virus Infection," *Journal of Virology*, 79(5): 2910-2919 (Mar. 2005).

U.S. Appl. No. 10/567,766, filed Dec. 29, 2006.

Bertram et al., "In situ gelling nasal inserts for influenza vaccine delivery," *Drug Development and Industrial Pharmacy*, 36(5): 581-593 (2010).

Miyamoto et al., "Effect of poly-L-arginine on the nasal absorption of FITC-dextran of different molecular weights and recombinant human granulocyte colony-stimulating factor (rhG-CSF) in rats," *International Journal of Pharmaceutics*, 226: 127-138 (2001).

Ichinohe et al., "Synthetic Double-Stranded RNA Poly(I:C) Combined with Mucosal Vaccine Protects against Influenza Virus Infection", *Journal of Virology*, 79(5): 2910-2919 (2005).

* cited by examiner

METHOD FOR PROPHYLAXIS OF INFLUENZA USING VACCINE FOR INTRANASAL ADMINISTRATION

TECHNICAL FIELD

The present invention relates to a vaccine for the prophylaxis of influenza, and a method for the prophylaxis of influenza.

BACKGROUND ART

Influenza is a viral infectious disease that repeatedly becomes epidemic with different antigen every year. The vaccines approved in Japan for the prophylaxis of influenza are those for subcutaneous administration. Since the vaccination induces an IgG antibody having a neutralizing activity in the serum, it is highly effective for preventing progression of the condition into a more severe one such as pneumonia and the like. In the upper airway mucosa, which is the infection site, however, IgA is the main prophylactic component. Since IgA is not induced by subcutaneous administration, the infection-preventive effect is not sufficient. Therefore, the development of an infection-preventive vaccine has been desired for a long time.

The present inventors have developed an influenza vaccine for mucosal administration comprising a double-stranded RNA and an influenza virus antigen, which is superior in the infection-preventive effect (WO2005/014038).

DISCLOSURE OF THE INVENTION

It is therefore an object of the present invention to provide a novel vaccine which is useful for the prophylaxis of influenza, and a method for the prophylaxis of influenza.

To achieve the above-mentioned object, the present inventors have tried to examine the effects of vaccines by adding various components, and completed the present invention.

Accordingly, the present invention provides the following.

[1] A vaccine composition for nasal mucosal administration, comprising an influenza virus antigen, polyriboinosinic polyribocytidylic acid (poly (I:C)) or a derivative thereof and a carboxyvinyl polymer.

[2] The composition of [1], wherein the aforementioned antigen is a subunit antigen or an inactivated antigen.

[3] The composition of [2], wherein the aforementioned subunit antigen comprises at least one subunit antigen selected from the group consisting of HA, NA, M1, M2, NP, PB1, PB2, PA and NS2 of influenza virus.

[4] The composition of [2], wherein the aforementioned subunit antigen comprises at least one subunit antigen selected from the group consisting of HA and NA.

[5] The composition of [1], wherein the aforementioned derivative is poly ($I:C_{12}U$).

[6] A method of preventing influenza, comprising a step of administering a vaccine composition comprising an effective amount of an influenza virus antigen and poly (I:C) or a derivative thereof, and a carboxyvinyl polymer at least once to the nasal mucosa of a subject in need thereof.

[7] The method of [6], wherein the aforementioned antigen is a subunit antigen or an inactivated antigen.

[8] The method of [7], wherein the aforementioned subunit antigen comprises at least one subunit antigen selected from the group consisting of HA, NA, M1, M2, NP, PB1, PB2, PA and NS2 of influenza virus.

[9] The method of [7], wherein the aforementioned subunit antigen comprises at least one subunit antigen selected from the group consisting of HA and NA.

[10] The method of [6], wherein the aforementioned derivative is poly ($I:C_{12}U$).

[11] The method of [6], wherein the aforementioned vaccine composition is administered at least twice.

[12] The method of [11], wherein the aforementioned vaccine composition is administered at an interval of at least 1 week.

The characteristics and the advantages of the present invention will be apparent from the detailed description of the invention below.

DETAILED DESCRIPTION OF THE INVENTION

Figure 1:
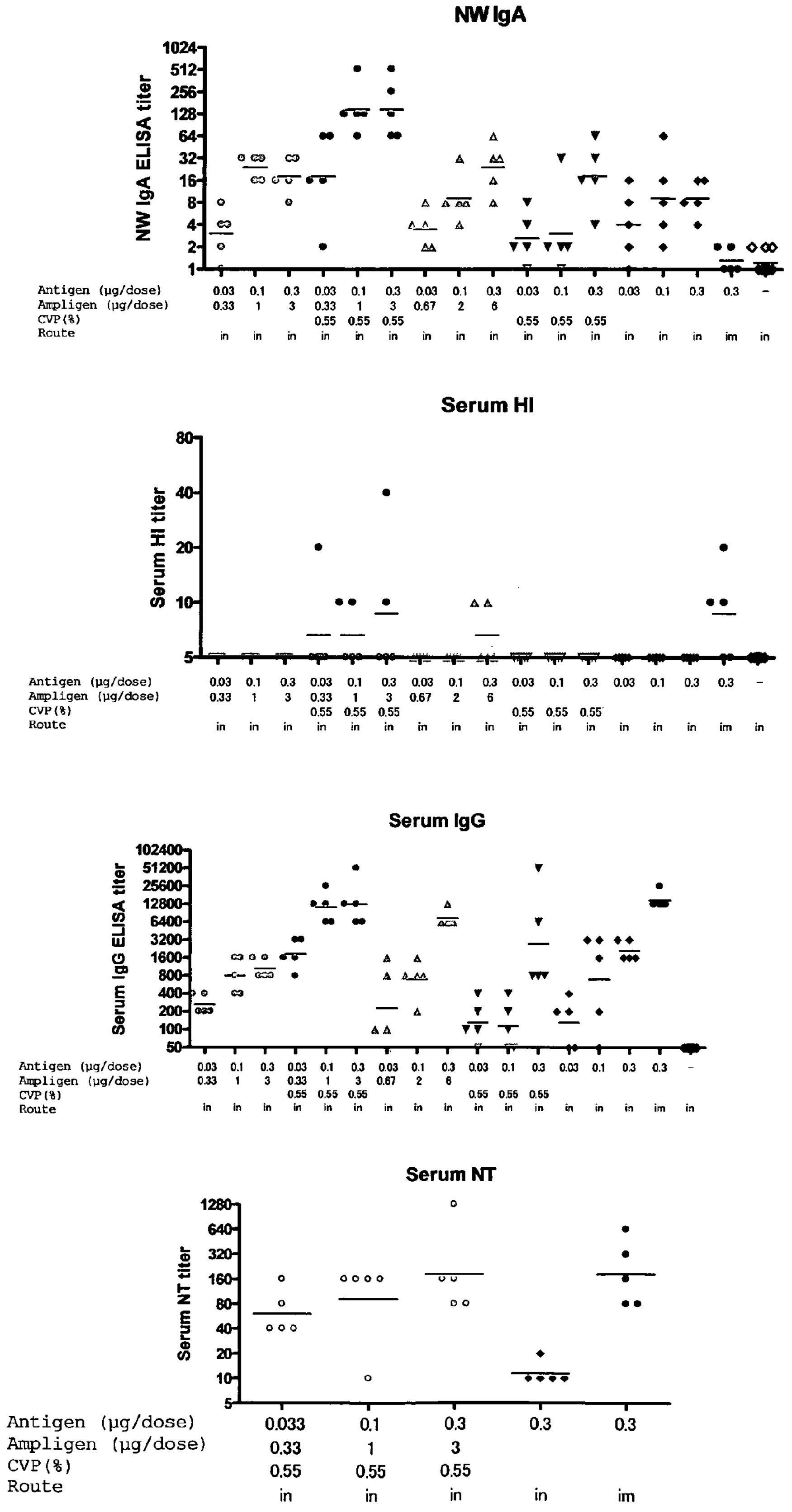
FIG. 1 shows an immune response in a nasal administration test of an influenza vaccine comprising Ampligen and a CVP base in combination.

In the present invention, the influenza virus includes any subtype known at present, and subtypes which will be isolated and identified in the future. Since no epidemic has been heretofore observed in human and human infection needs to be effectively prevented hereafter, the influenza virus is preferably a subtype consisting of a combination of a type selected from H1-H16 excluding H1 and H3 (i.e., H2 and H4-16) and a type selected from N1-N9. These subtypes are also called new type of influenza virus. The aforementioned subtype is more preferably a subtype consisting of a combination of a type selected from H5, H7 and H9 and a type selected from N1-N9. The influenza virus may be one type of strain belonging to the same subtype, or two or more types of strains belonging to the same subtype, or two or more types of strains belonging to different subtypes.

The influenza virus antigen contained in the vaccine composition of the present invention is largely divided into an inactivated antigen and a subunit antigen.

The term "inactivated antigen" as used herein refers to an antigen deprived of infectivity, used as a vaccine antigen; such antigens include, but are not limited to, complete virus particle virions, incomplete virus particles, virion-constituting particles, virus non-structural proteins, antigens that protect against infections, neutralizing reaction epitopes and the like. The term "inactivated antigen" as used herein refers to an antigen deprived of infectivity, but retaining immunogenicity; when such an antigen is used as a vaccine, it is called an "inactivated vaccine." Examples of the inactivation methods of antigens include, but are not limited to, physical (e.g., X-ray irradiation, heat, ultrasound), chemical (formalin, mercury, alcohol, chlorine) or other procedures. Subunit antigen per se also falls within the definition of inactivated antigen because they have usually lost infectivity. Alternatively, a killed virus may be used.

The term "subunit antigen" as used herein refers to a component derived from an influenza virus. The subunit antigen includes hemagglutinin (HA), neuraminidase (NA), matrices (M1, M2), non-structures (NS), polymerases (PB1, PB2: basic polymerases 1 and 2, acidic polymerase (PA)), nuclear proteins (NP) and the like, with preference given to HA or NA, which is exposed to the surface of the virus particle. Currently known types of HA are HA1 to HA16, and known types of NA are NA1 to NA9. The subunit antigen may be purified from a pathogen such as a naturally occurring virus, or may be prepared by a synthetic or recombinant technology. Such methods are well known and in common use in the art, and can be performed using commercially available equipment, reagents, vectors and the like.

The amount of the influenza virus antigen to be contained in the vaccine composition of the present invention is not particularly limited as long as it is sufficient to produce secretary IgA, and can be appropriately determined in consideration of the ratio to the below-mentioned poly (I:C) or a derivative thereof. When HA is used as an antigen, for example, its concentration is preferably 10-500 μg HA/mL (based on HA), more preferably 30-400 μg HA/mL (based on HA). The aforementioned concentration is obtained by measuring the concentration of HA protein.

Poly(I:C) as contained in the vaccine composition of the present invention is a double-stranded RNA (dsRNA) comprising polyinosinic acid (pI) and polycitidic acid (pC).

A derivative of poly (I:C) refers to a mismatched dsRNA obtained by modifying the specific configuration of poly (I:C) through the introduction of unpaired bases thereinto, and includes poly (I:$C_x$U), poly ($I_x$U:C) (where x is on average a number from 3 to 40) and the like. Preferably, a derivative of poly (l:C) is poly (I:$C_{12}$U) or poly (C:$I_{12}$U), which is commercially available under the trade name Ampligen™.

Poly (l:C) or a derivative thereof is supplied in a size sufficient to produce secretory IgA. Examples of such sizes include 100 bp or more, with preference given to sizes of 300 bp or more, which sizes, however, are not to be construed as limiting. Examples of the upper limit of size include, but are not limited to, $10^8$ bp.

Poly (I:C) or a derivative thereof is present at a concentration sufficient to produce secretory IgA. Such a concentration of poly (I:C) or a derivative thereof is, for example, 0.1 to 10 mg/mL, more preferably 0.5 to 2 mg/mL, and still more preferably about 1 mg/mL (e.g., 0.8 to 1.2 mg/mL).

The weight ratio of the influenza virus antigen and poly (I:C) or a derivative thereof to be contained in the vaccine composition of the present invention is recommended to be 1:1-1:50.

A carboxyvinyl polymer (CVP) contained in the vaccine composition of the present invention is a hydrophilic polymer which is produced by polymerization of acrylic acid as the main monomer component and includes conventional ones such as Carbopol™ commercially available from Lubrizol Advanced Materials, Inc. US and the like. The concentration of CVP used in the present invention is generally in the range of 0.1-2.0% by weight.

The vaccine composition of the present invention may contain a water-soluble basic substance for the purpose of thickening CVP. The water-soluble basic substance includes, for example, inorganic bases (e.g., sodium hydroxide, potassium hydroxide, ammonia, etc.), and organic bases such as alkylamines (e.g., methylamine, ethylamine, propylamine, etc.), dialkylamines (e.g., dimethylamine, diethylamine, dipropylamine, etc.), trialkylamines (e.g., trimethylamine, triethylamine, tripropylamine, etc.), alkanolamines (e.g., methanolamine, ethanolamine, propanolamine, etc.), dialkanolamines (e.g., dimethanolamine, diethanolamine, dipropanolamine, etc.), trialkanolamines (e.g., trimethanolamine, triethanolamine, tripropanolamine, etc.), amino acids (e.g., arginine, lysine, ornithine, etc.) and the like. These water-soluble bases are used in an amount which is necessary for neutralization to adjust the pH value of CVP aqueous solution to a desired pH.

The pH value of the vaccine composition of the present invention is adjusted to the desired pH with a water-soluble basic substance or other pH adjustors taking into consideration the stability or absorption of an influenza virus antigen. Preferable pH range is 6.0-8.0.

Adjustment of the viscosity can be performed depending on the vaccine dosage form. For example, CVP corresponding to 0.1-2.0% by weight is thickened with a water-soluble basic substance and the viscosity is adjusted by applying an outside shearing force, or the viscosity is adjusted with a viscosity modulating agent and an outside shearing force, whereby a base managed to suit the spray angle and spray density from a sprayer is prepared. Thereafter, an influenza virus antigen and poly (I:C) are admixed.

The vaccine composition of the present invention may contain a suitable active medicament, diluent, bactericide, preservative, surfactant, stabilizer and the like which can be used together with the vaccine.

The present invention relates to a method of preventing influenza, comprising a step of administering a vaccine composition comprising an effective amount of an influenza virus antigen and poly (I:C) or a derivative thereof, and a carboxyvinyl polymer at least once to the nasal mucosa of a subject in need thereof.

The subject of administration of the vaccine composition of the present invention includes, but is not limited to, mammals including human, birds and the like.

Nasal mucosal administration of the vaccine composition can be performed in an appropriate form. Various methods such as spraying, coating, or direct dripping of a vaccine liquid can be used.

Administration frequency of the vaccine composition of the present invention is at least once, preferably at least twice, in view of the effectiveness. Additional administration is sometimes called booster immunization. Booster immunization makes it possible to achieve a higher infection-protective effect. The interval of booster immunization is recommended to be at least 1 week, preferably 1 to 4 weeks.

The present invention is hereinafter described in more detail by means of the following examples, which, however, are not to be construed as limiting the present invention.

EXAMPLE 1

Nasal Administration Test of Whole Virion Vaccine Containing Ampligen and CVP in Combination for New Type of Influenza, Using Mouse In the development of an influenza vaccine for nasal administration, a vaccine corresponding to pandemic influenza is highly important and highly urgent as compared to vaccine for seasonal influenza, and needs to be preferentially developed. Therefore, a sample vaccine containing a vaccine for new type of influenza (PR8-IBCDC-RG2 strain: attenuated virus strain of A/Indo/5/2005 (H5N1)) and Ampligen in a 10-fold amount of HA antigen was prepared in the same manner as for seasonal influenza HA vaccine. The sample vaccine contained, as an additive for enhancing an immune response in the nasal mucosa by delaying the clearance of vaccine from the nasal mucosa, a CVP base [mixture of 0.55% CVP, 1.2% L-arginine, 1% glycerin] also applied to allergy medicines.

For a nasal administration test, 7-week-old female BALB/c mice were used (5 per group), and antigen was administered at 0.033-1 μg HA/head. As a comparison control, a group for which Ampligen was added to vaccine in a 10-fold amount of HA antigen and CVP base was not added, a group for which Ampligen was added to vaccine in a 20-fold amount of HA antigen and CVP base was not added, a group for which CVP alone was added to vaccine, a group to which vaccine without addition was nasally administered, and a group to which vaccine without addition was intramuscularly administered were prepared. The vaccine was administered twice at 3-week intervals, and nasal washings and serum were recovered 2 weeks after booster. Specific IgA-ELISA antibody titer of the nasal washings was measured, and the antibody titers of hemagglutination inhibition (HI), neutralizing antibody and specific IgG-ELISA of the serum were measured. Since the sample vaccine had high viscosity, the administration method was changed from conventional nasal drip using a micropipette to injection by inserting about 4 mm of a blunt needle (27G, 0.4 mm×38 mm) set to a microsyringe.

The results are shown in Tables 1-9.

TABLE 1

A/Hiroshima HA vaccine + Poly (I:C) or Ampligen (lot comparison)

| group | antigen | administration route | dose | numbers/group | antigen (μg HA or ptn) | Poly (I:C) | Ampligen (new) |
|---|---|---|---|---|---|---|---|
| 1 | A/Hiroshima/ | in | 2 μl to each | 5 | 0.1 | | |
| 2 | 52/2005 | | nasal cavity | | 0.1 | 0.1 | |
| 3 | (H3N2) HA | | | | 0.1 | 1 | |
| 4 | vaccine | | 2.7 μl to each nasal cavity | | 0.1 | 10 | |
| 5 | | | | | 0.1 | | 0.1 |
| 6 | | | | | 0.1 | | 1 |
| 7 | | | | | 0.1 | | 10 |
| 8 | | sc | 100 | | 0.1 | | |
| 9 | whole virion | in | | | 0.2 | | |
| 10 | none (control) | | | 10 | | | |

1st: 1/28 BALB/c mice (7w♀)
2nd: 2/18
Sampling: 2/28
Antigen was A/Hiroshima/52/2005(H3N2) HA vaccine FTHAG0712 (1205 μg HA/mL) or whole virion vaccine (344 μg ptn/mL)
poly(I:C)[SIGMA P-0913] was adjusted to 1.88 mg/mL
Ampligen (new) was Lot0701HE

TABLE 2 exp. A/Hiroshima HA vaccine + Poly (I:C) or Ampligen NW IgA ELISA

| group | | 1 | 2 | 3 | 4 | 5 | 6 | 7 | 8 | 9 | 10 |
|---|---|---|---|---|---|---|---|---|---|---|---|
| antigen | | A/Hiroshima/52/2005 (H3N2) HA vaccine | | | | | | | | whole virion | none (control) |
| administration route | | in | | | | | | | sc | in | |
| dose | | 2 μl to each nostril (nasal cavity) | | | 2.7 μl to each nostril (nasal cavity) | 2 μl to each nostril (nasal cavity) | | | 100 μl | 2 μl to each nostril (nasal cavity) | |
| numbers/group | | 5 | | | | | | | | | 10 |
| antigen (μg HA or ptn) | | 0.1 | 0.1 | 0.1 | 0.1 | 0.1 | 0.1 | 0.1 | 0.1 | 0.2 | |
| adjuvant | Poly (I:C) | | 0.1 | 1 | 10 | | | | | | |
| (μg/head) | Ampligen (new) | | | | | 0.1 | 1 | 10 | | | |
| animal | 1 | 1 | 1 | 1 | 16 | 1 | 1 | 128 | 1 | 64 | 1 |
| No. | 2 | 1 | 32 | 16 | 16 | 128 | 4 | 32 | 1 | 8 | 1 |
| | 3 | 1 | 2 | 16 | 128 | 32 | 32 | 4 | 1 | 8 | 1 |
| | 4 | 1 | 16 | 32 | 256 | 32 | 8 | 16 | 1 | 32 | 1 |
| | 5 | 1 | 64 | 32 | 64 | 2 | 2 | 16 | 1 | 32 | 1 |
| geometric mean | | 1.0 | 9.2 | 12.1 | 55.7 | 12.1 | 4.6 | 21.1 | 1.0 | 21.1 | 1.0 |
| SD | | 0.0 | 26.2 | 13.0 | 100.6 | 52.0 | 12.9 | 50.6 | 0.0 | 23.0 | 0.0 |
| geometric mean titer (GMT, 2^n) | | 0.0 | 3.2 | 3.6 | 5.8 | 3.6 | 2.2 | 4.4 | 0.0 | 4.4 | 0.0 |
| positive conversion ratio (≥32, %) | | 0.0 | 40.0 | 40.0 | 60.0 | 60.0 | 20.0 | 40.0 | 0.0 | 60.0 | 0.0 |

TABLE 3 exp. A/Hiroshima HA vaccine + Poly (I:C) or Ampligen Serum IgG

| group | 1 | 2 | 3 | 4 | 5 | 6 | 7 | 8 | 9 | 10 |
|---|---|---|---|---|---|---|---|---|---|---|
| antigen | A/Hiroshima/52/2005 (H3N2) HA vaccine FTHAG0712 | | | | | | | | whole virion | none (control) |
| administration route | in | | | | | | | sc | in | |
| dose | 2 μl to each nostril (nasal cavity) | | | 2.7 μl to each nostril (nasal cavity) | 2 μl to each nostril (nasal cavity) | | | 100 μl | 2 μl to each nostril (nasal cavity) | |
| numbers/group | 5 | | | | | | | | | 10 |
| antigen (μg HA or ptn) | 0.1 | 0.1 | 0.1 | 0.1 | 0.1 | 0.1 | 0.1 | 0.1 | 0.2 | |
| Poly (I:C) | | 0.1 | 1 | 10 | | | | | | |
| Ampligen (new) | | | | | 0.1 | 1 | 10 | | | |
| animal No. 1 | 50 | 50 | 100 | 6400 | 100 | 50 | 1600 | 51200 | 1600 | 50 |
| 2 | 50 | 800 | 200 | 400 | 400 | 400 | 800 | 51200 | 400 | 50 |
| 3 | 50 | 400 | 1600 | 6400 | 6400 | 1600 | 100 | 51200 | 200 | 50 |
| 4 | 50 | 200 | 800 | 3200 | 200 | 6400 | 50 | 25600 | 400 | 100 |
| 5 | 50 | 400 | 400 | 800 | 200 | 50 | 800 | 25600 | 1600 | 50 |
| geometric mean | 50.0 | 263.9 | 400.0 | 2111.2 | 400.0 | 400.0 | 348.2 | 38802.3 | 606.3 | 53.6 |
| SD | 0.0 | 282.0 | 609.9 | 2906.5 | 2763.7 | 2703.5 | 634.0 | 14021.7 | 698.6 | 15.8 |
| geometric mean titer (GMT, 2^n) | 5.6 | 8.0 | 8.6 | 11.0 | 8.6 | 8.6 | 8.4 | 15.2 | 9.2 | 5.7 |

TABLE 4 exp. A/Hiroshima HA vaccine + Poly (I:C) or Ampligen Serum HI

| group | 1 | 2 | 3 | 4 | 5 | 6 | 7 | 8 | 9 | 10 |
|---|---|---|---|---|---|---|---|---|---|---|
| antigen | A/Hiroshima/52/2005 (H3N2) HA vaccine | | | | | | | | whole virion | none (control) |
| administration route | in | | | | | | | sc | in | |
| dose | 2 μl to each nostril (nasal cavity) | | | 2.7 μl to each nostril (nasal cavity) | 2 μl to each nostril (nasal cavity) | | | 100 μl | 2 μl to each nostril (nasal cavity) | |
| numbers/group | 5 | | | | | | | | | 10 |
| antigen (μg HA or ptn) | 0.1 | 0.1 | 0.1 | 0.1 | 0.1 | 0.1 | 0.1 | 0.1 | 0.2 | |
| Poly (I:C) | | 0.1 | 1 | 10 | | | | | | |
| Ampligen (new) | | | | | 0.1 | 1 | 10 | | | |
| animal No. 1 | 5 | 5 | 5 | 40 | 5 | 5 | 5 | 160 | 5 | 5 |
| 2 | 5 | 5 | 5 | 5 | 5 | 5 | 5 | 320 | 5 | 5 |
| 3 | 5 | 5 | 5 | 40 | 5 | 5 | 5 | 320 | 5 | 5 |
| 4 | 5 | 5 | 5 | 20 | 5 | 10 | 5 | 160 | 5 | 5 |
| 5 | 5 | 5 | 5 | 5 | 5 | 10 | 5 | 80 | 5 | 5 |
| geometric mean | 5.0 | 5.0 | 5.0 | 15.2 | 5.0 | 6.6 | 5.0 | 183.8 | 5.0 | 5.0 |
| SD | 0.0 | 0.0 | 0.0 | 17.5 | 0.0 | 2.7 | 0.0 | 107.3 | 0.0 | 0.0 |
| geometric mean titer (GMT, 2^n) | 2.3 | 2.3 | 2.3 | 3.9 | 2.3 | 2.7 | 2.3 | 7.5 | 2.3 | 2.3 |
| seroconversion rate (≥40, %) | 0.0 | 0.0 | 0.0 | 40.0 | 0.0 | 0.0 | 0.0 | 100.0 | 0.0 | 0.0 |

TABLE 5

Ampligen pharmacological effect preliminary test: H5 Indonesia whole virion (2008 Sep. 25) test group constitution

| group | antigen (μg/dose) | Ampligen (μg/dose) | CVP (%) | n | adminis-tration route | dose (μl) | note |
|---|---|---|---|---|---|---|---|
| 1 | 0.3 | 3.00 | | 5 | in | 2.0 | antigen: |
| 2 | 0.1 | 1.00 | | 5 | in | 2.0 | Ampligen = |
| 3 | 0.033 | 0.33 | | 5 | in | 2.0 | 1:10 |
| 4 | 0.3 | 3.00 | 0.55 | 5 | in | 2.0 | antigen: |
| 5 | 0.1 | 1.00 | 0.55 | 5 | in | 2.0 | Ampligen = |
| 6 | 0.033 | 0.33 | 0.55 | 5 | in | 2.0 | 1:10 + CVP |
| 7 | 0.3 | 6.00 | | 5 | in | 2.0 | antigen: |
| 8 | 0.1 | 2.00 | | 5 | in | 2.0 | Ampligen = |
| 9 | 0.033 | 0.67 | | 5 | in | 2.0 | 1:10 |
| 10 | 0.3 | | 0.55 | 5 | in | 2.0 | antigen + |
| 11 | 0.1 | | 0.55 | 5 | in | 2.0 | CVP |
| 12 | 0.033 | | 0.55 | 5 | in | 2.0 | |
| 13 | 0.3 | | | 5 | in | 2.0 | antigen |
| 14 | 0.1 | | | 5 | in | 2.0 | alone |
| 15 | 0.033 | | | 5 | in | 2.0 | |
| 16 | 0.3 | | | 5 | im | 50.0 | antigen alone, |

TABLE 5-continued

Ampligen pharmacological effect preliminary test: H5 Indonesia whole virion (2008 Sep. 25) test group constitution

| group | antigen (μg/dose) | Ampligen (μg/dose) | CVP (%) | n | adminis-tration route | dose (μl) | note |
|---|---|---|---|---|---|---|---|
| | | | | | | | intra-muscular control |
| 17 | | | | 10 | in | 2.0 | saline control |

2008 Sep. 30 1st immunization

2008 Oct. 21 2nd immunization

2008 Nov. 4 Sampling

Antigen was attenuated virus strain of PR8-IBCDC-RG2 strain: A/Indo/5/2005(H5N1), Lot FPBMW0612-0 3110 μg PTN/mL. about 1048 μg HA/mL))

Ampligen is manufactured by Hemispherx, Lot R-01: 45.7 mg/mL

CVP is manufactured by Toko Yakuhin Kogyo, Lot No. INF-9B8, base for preparation (#03-01)

Remark 1: prepared for 300 mice antigen: 300 mice × 0.3 μg/head/1.048 μg/μl = 85.9 μl BALB/c mice, 7 w ♀, were used.

TABLE 6

| Ampligenpharmacological effect preliminary test: H5 Indonesia whole virion (2008 Sep. 25-) NW IgA (2008 Nov. 6) | | | | | | | | | | | | | | | | | | |
|---|---|---|---|---|---|---|---|---|---|---|---|---|---|---|---|---|---|---|
| group | | 1 | 2 | 3 | 4 | 5 | 6 | 7 | 8 | 9 | 10 | 11 | 12 | 13 | 14 | 15 | 16 | 17 |
| antigen (μg/dose) | | 0.3 | 0.1 | 0.033 | 0.3 | 0.1 | 0.033 | 0.3 | 0.1 | 0.033 | 0.3 | 0.1 | 0.033 | 0.3 | 0.1 | 0.033 | 0.3 | |
| Ampligen (μg/dose) | | 3.00 | 1.00 | 0.33 | 3.00 | 1.00 | 0.33 | 6.00 | 2.00 | 0.67 | | | | | | | | |
| CVP (%) | | | | | 0.55 | 0.55 | 0.55 | | | | 0.55 | 0.55 | 0.55 | | | | | |
| administration method | | in | in | in | in | in | in | in | in | in | in | in | in | in | in | in | im | in |
| animal | 1 | 32 | 32 | 4 | 256 | 128 | 16 | 8 | 8 | 4 | 16 | 32 | 8 | 16 | 16 | 1 | 1 | 1 |
| No. | 2 | 16 | 16 | 8 | 512 | 128 | 16 | 32 | 4 | 4 | 32 | 2 | 2 | 4 | 8 | 8 | 1 | 1 |
| | 3 | 32 | 32 | 4 | 128 | 128 | 2 | 16 | 8 | 2 | 16 | 2 | 1 | 16 | 2 | 4 | 1 | 2 |
| | 4 | 16 | 16 | 2 | 64 | 512 | 64 | 32 | 32 | 2 | 64 | 2 | 2 | 8 | 4 | 16 | 2 | 2 |
| | 5 | 8 | 32 | 1 | 64 | 64 | 64 | 64 | 8 | 8 | 4 | 1 | 4 | 8 | 64 | 2 | 2 | 2 |
| geometric mean titer (GMT) | | 18.4 | 24.3 | 3.0 | 147.0 | 147.0 | 18.4 | 24.3 | 9.2 | 3.5 | 18.4 | 3.0 | 2.6 | 9.2 | 9.2 | 4.0 | 1.3 | 1.5 |
| mean titer (2^n) | | 4.2 | 4.6 | 1.6 | 7.2 | 7.2 | 4.2 | 4.6 | 3.2 | 1.8 | 4.2 | 1.6 | 1.4 | 3.2 | 3.2 | 2.0 | 0.4 | 0.6 |
| positive conversion ratio (titer ≥32, %) | | 40 | 60 | 0 | 100 | 100 | 40 | 60 | 20 | 0 | 40 | 20 | 0 | 0 | 20 | 0 | 0 | 0 |

TABLE 7

| Ampligen pharmacological effect preliminary test: H5 Indonesia whole virion (2008 Sep. 25-) Serum NT (2008 Nov. 19) | | | | | | |
|---|---|---|---|---|---|---|
| | | group | | | | |
| | | 4 | 5 | 6 | 13 | 16 |
| antigen (μg/dose) | | 0.3 | 0.1 | 0.033 | 0.3 | 0.3 |
| Ampligen (μg/dose) | | 3.00 | 1.00 | 0.33 | | |
| CVP (%) | | 0.55 | 0.55 | 0.55 | | |
| Poly L-Arg (μg/dose) | | | | | | |
| administration method | | in | in | in | in | im |
| animal No. | 1 | 80 | 160 | 80 | 20 | 160 |
| | 2 | 1280 | 10 | 40 | 10 | 80 |
| | 3 | 80 | 160 | 40 | 10 | 320 |
| | 4 | 160 | 160 | 160 | 10 | 80 |
| | 5 | 160 | 160 | 40 | 10 | 640 |
| geometric mean titer (GMT) | | 183.8 | 91.9 | 60.6 | 11.5 | 183.8 |
| mean titer (2^n) | | 7.5 | 6.5 | 5.9 | 3.5 | 7.5 |

TABLE 8

| Ampligen pharmacological effect preliminary test: H5 Indonesia whole virion (2008 Sep. 25-) Serum HI (2008 Nov.) | | | | | | | | | | | | | | | | | | |
|---|---|---|---|---|---|---|---|---|---|---|---|---|---|---|---|---|---|---|
| | | group | | | | | | | | | | | | | | | | |
| | | 1 | 2 | 3 | 4 | 5 | 6 | 7 | 8 | 9 | 10 | 11 | 12 | 13 | 14 | 15 | 16 | 17 |
| antigen (μg/dose) | | 0.3 | 0.1 | 0.033 | 0.3 | 0.1 | 0.033 | 0.3 | 0.1 | 0.033 | 0.3 | 0.1 | 0.033 | 0.3 | 0.1 | 0.033 | 0.3 | |
| Ampligen (μg/dose) | | 3.00 | 1.00 | 0.33 | 3.00 | 1.00 | 0.33 | 6.00 | 2.00 | 0.67 | | | | | | | | |
| CVP (%) | | | | | 0.55 | 0.55 | 0.55 | | | | 0.55 | 0.55 | 0.55 | | | | | |
| administration method | | in | in | in | in | in | in | in | in | in | in | in | in | in | in | in | im | in |
| animal No. | 1 | 5 | 5 | 5 | 5 | 10 | 5 | 5 | 5 | 5 | 5 | 5 | 5 | 5 | 5 | 5 | 10 | 5 |
| | 2 | 5 | 5 | 5 | 40 | 5 | 5 | 5 | 5 | 5 | 5 | 5 | 5 | 5 | 5 | 5 | 5 | 5 |
| | 3 | 5 | 5 | 5 | 5 | 5 | 5 | 5 | 5 | 5 | 5 | 5 | 5 | 5 | 5 | 5 | 20 | 5 |
| | 4 | 5 | 5 | 5 | 10 | 10 | 20 | 10 | 5 | 5 | 5 | 5 | 5 | 5 | 5 | 5 | 5 | 5 |
| | 5 | 5 | 5 | 5 | 5 | 5 | 5 | 10 | 5 | 5 | 5 | 5 | 5 | 5 | 5 | 5 | 10 | 5 |
| geometric mean titer (GMT) | | 5.0 | 5.0 | 5.0 | 8.7 | 6.6 | 6.6 | 6.6 | 5.0 | 5.0 | 5.0 | 5.0 | 5.0 | 5.0 | 5.0 | 5.0 | 8.7 | 5.0 |
| mean titer (2^n) | | 2.3 | 2.3 | 2.3 | 3.1 | 2.7 | 2.7 | 2.7 | 2.3 | 2.3 | 2.3 | 2.3 | 2.3 | 2.3 | 2.3 | 2.3 | 3.1 | 2.3 |
| seroconversion rate (≥40, %) | | 0 | 0 | 0 | 20 | 0 | 0 | 0 | 0 | 0 | 0 | 0 | 0 | 0 | 0 | 0 | 0 | 0 |

TABLE 9

| Ampligen pharmacological effect preliminary test: H5 Indonesia whole virion (2008 Sep. 25-) Serum IgG (2008 Nov. 6) | | | | | | | | | |
|---|---|---|---|---|---|---|---|---|---|
| | group | | | | | | | | |
| | 1 | 2 | 3 | 4 | 5 | 6 | 7 | 8 | 9 |
| antigen (μg/dose) | 0.3 | 0.1 | 0.033 | 0.3 | 0.1 | 0.033 | 0.3 | 0.1 | 0.033 |
| Ampligen (μg/dose) | 3.00 | 1.00 | 0.33 | 3.00 | 1.00 | 0.33 | 6.00 | 2.00 | 0.67 |
| CVP (%) | | | | 0.55 | 0.55 | 0.55 | | | |

TABLE 9-continued

Ampligen pharmacological effect preliminary test: H5 Indonesia whole virion (2008 Sep. 25-)
Serum IgG (2008 Nov. 6)

| | | | | | | | | | | |
|---|---|---|---|---|---|---|---|---|---|---|
| administration method | | in | in | in | in | in | in | in | in | in |
| animal No. | 1 | 1600 | 1600 | 400 | 12800 | 6400 | 1600 | 6400 | 200 | 50 |
| | 2 | 1600 | 1600 | 400 | 51200 | 6400 | 800 | 6400 | 800 | 800 |
| | 3 | 800 | 800 | 200 | 6400 | 12800 | 1600 | 6400 | 800 | 100 |
| | 4 | 800 | 400 | 200 | 6400 | 25600 | 3200 | 6400 | 1600 | 100 |
| | 5 | 800 | 400 | 200 | 12800 | 12800 | 3200 | 12800 | 800 | 1600 |
| geometric mean titer (GMT) | | 1055.6 | 800.0 | 263.9 | 12800.0 | 11143.0 | 1837.9 | 7351.7 | 696.4 | 229.7 |
| mean titer (2^n) | | 10.0 | 9.6 | 8.0 | 13.6 | 13.4 | 10.8 | 12.8 | 9.4 | 7.8 |
| positive conversion ratio (titer ≥32, %) | | 100 | 100 | 100 | 100 | 100 | 100 | 100 | 100 | 100 |

| | | group | | | | | | | |
|---|---|---|---|---|---|---|---|---|---|
| | | 10 | 11 | 12 | 13 | 14 | 15 | 16 | 17 |
| antigen (μg/dose) | | 0.3 | 0.1 | 0.033 | 0.3 | 0.1 | 0.033 | 0.3 | |
| Ampligen (μg/dose) | | | | | | | | | |
| CVP (%) | | 0.55 | 0.55 | 0.55 | | | | | |
| administration method | | in | in | in | in | in | in | im | in |
| animal No. | 1 | 800 | 400 | 400 | 1600 | 200 | 50 | 12800 | 50 |
| | 2 | 6400 | 50 | 50 | 3200 | 3200 | 200 | 12800 | 50 |
| | 3 | 51200 | 50 | 100 | 1600 | 50 | 200 | 25600 | 50 |
| | 4 | 800 | 200 | 100 | 3200 | 1600 | 400 | 12800 | 50 |
| | 5 | 800 | 100 | 200 | 1600 | 3200 | 50 | 12800 | 50 |
| geometric mean titer (GMT) | | 2785.8 | 114.9 | 132.0 | 2111.2 | 696.4 | 132.0 | 14703.3 | 50.0 |
| mean titer (2^n) | | 11.4 | 6.8 | 7.0 | 11.0 | 9.4 | 7.0 | 13.8 | 5.6 |
| positive conversion ratio (titer ≥32, %) | | 100 | 100 | 100 | 100 | 100 | 100 | 100 | 200 |

(Results)

Nasal Administration Test of Whole Virion Vaccine for New Type of Influenza, Containing Ampligen and CVP Base in Combination, and Using Mouse A remarkable immunoenhancing effect was confirmed in the mucosa and serum in the group administered with a vaccine containing Ampligen and a CVP base in combination, which was not found in the group administered with Ampligen alone. The specific IgG, HI and neutralizing antibody titer (NT) of the serum increased to levels equivalent to those of the intramuscular injection group (no adjuvant).

A sample pandemic influenza vaccine containing, as an additive for enhancing an immune response in the nasal mucosa, a CVP base also applied to allergy medicines in combination, was prepared and used for a nasal administration test.

We investigated the convenience of nasal administration method at this time and obtained unexpected effects of a remarkably improved immune response of the nasal mucosa, a specific antibody titer of the serum, which is equivalent to that of intramuscular injection without adjuvant, and the like. Hence, a more practical vaccine was obtained.

EXAMPLE 2

Evaluation System Via Transnasal Immunity in Mouse (Consideration of Optimal Dose and Administration Frequency for Mouse)

The optimal dose and administration frequency for mouse were examined based on the measurements of serum specific IgG antibody titer and HI antibody titer after addition of Ampligen, CVP and the like to an antigen, and the comparison with existing vaccines having known composition and known administration method, and using a "new type influenza virus antigen at high concentration".

(Materials)

1. New type influenza vaccine stock solution and virus for evaluation of cross-reactive antibody titer:

new type influenza vaccine stock solution: lot No.; FPBMW0612-c (protein concentration: 3110 μg/mL, HA content 992 μg HA/mL, origin virus strain: A/Indo/5/2005 (H5N1)/PR8-IBCDC-RG2) (The Research Foundation for Microbial Diseases of Osaka University)

2. Original strain of virus and inactivated vaccine antigen: for measurement of specific antibody titer:

A/Indo/5/2005(H5N1)/PR8-IBCDC-RG2 strain: attenuated strain (clade 2.1) of A/Indonesia/5/2005 (H5N1) for measurement of cross-reactive antibody titer:

A/Anhui/01/2005(H5N1)/PR8-IBCDC-RG5 strain: attenuated strain (clade 2.3) of A/Anhui/01/2005 (H5N1)

A/bar-headed goose/Qinghai/1A/2005 strain: attenuated strain (clade 2.2) of A/Qinghai/1A/2005 (H5N1)

NIBRG-14 strain: attenuated strain (clade 1) of A/Vietnam/1194/2004 (H5N1)

3. Adjuvant:

Ampligen®: containing Ampligen (2.5 mg/mL) manufactured by Hemispherx

4. Test method

Figure 2:
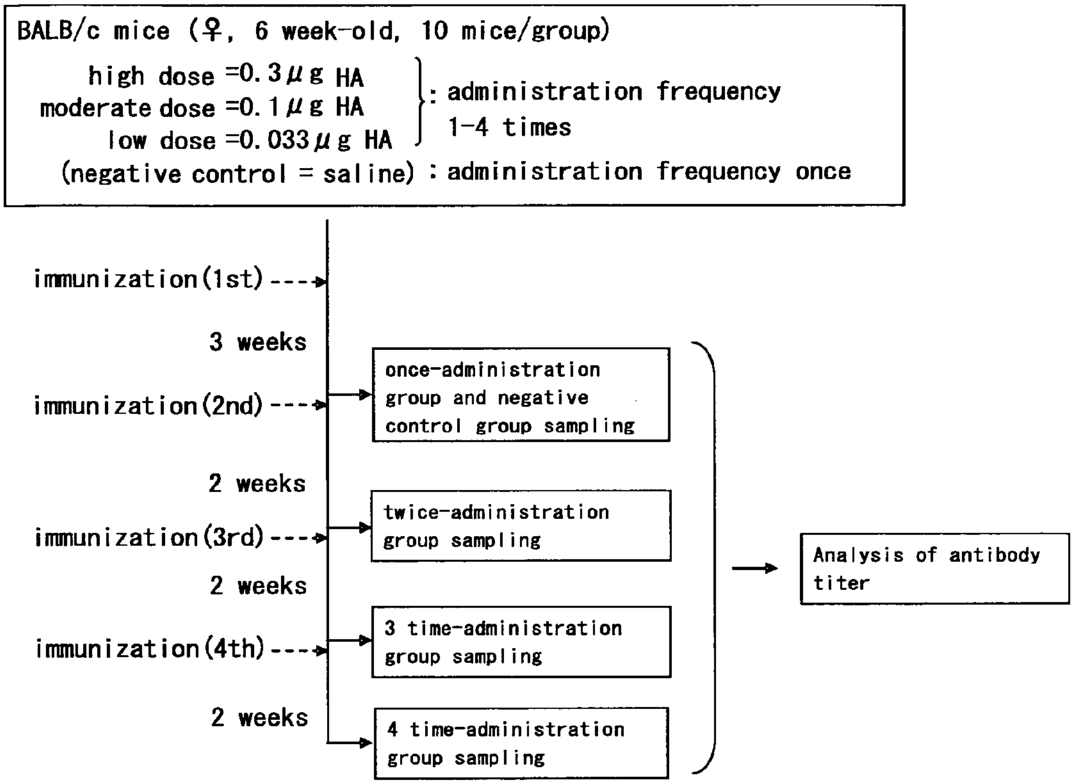
FIG. 2 is a flow chart of mouse immunity test in Example 2.

FIG. 2 shows a schematic view of test flows.

A vaccine containing A/Indo/5/2005 (H5N1)/PR8-IBCDC-RG2 virus antigen (obtained by adding Ampligen to a 20-fold concentration of HA antigen, and adding CVP base (1.1% carboxyvinyl polymer, 2.4% L-arginine, 2.0% glycerol) to 50.0 v/v % of the total amount) was transnasally administered to BALB/c mice and samples (nasal swab and serum) were taken 3 weeks later. In this case, samples were not taken from a part of the mice, and booster was given thereto one to three times. The interval between the boosters for mice subjected to two or three times of boosters was 2 weeks. Samples were taken at 2 weeks from the last booster, and immune response was confirmed when all samples were taken. As comparison controls for the confirmation of the effects of Ampligen and CVP base added, a non-addition vaccine transnasal administration group (high dose, medium dose, low dose) with the same antigen dose but free of Ampligen and CVP base and a negative control group (transnasal administration (once) of saline) were set, and a non-addition vaccine intramuscular administration group (high dose) was set for comparison with vaccines having known dosage form and known administration method. From the above-mentioned test, the relationship between dose and administration frequency, and immune response was evaluated. In addition, immune response with a virus strain having different antigenicity was also investigated to obtain findings as to the cross-reactivity.

5. Animals and vaccine (Table 10)

test animal: BALB/c mouse (♀, 6-week-old when the test was started), 10 mice/group trial vaccine for test consideration and adjuvant dose:

high dose group: [0.3 μg HA+6 μg Ampligen]/dose medium dose group: [0.1 μg HA+2 μg Ampligen]/dose low dose group: [0.033 μg HA+0.66 μg Ampligen]/dose As negative control, a saline administration group was set. In addition, for confirmation of effects of vaccine addition, non-addition vaccine transnasal administration group (high dose, medium dose, low dose) with the same antigen dose but free of Ampligen and CVP base was set, and an intramuscular administration group (high dose) was set for the comparison with conventional vaccines (known dosage form•administration method).

vaccine composition:

high dose group: [vaccine 0.3 μL+Ampligen 2.4 μL+CVP base 2.5 μL]/dose medium dose group: [vaccine 0.1 μL+Ampligen 0.8 μL+M/75 PBS (PH 7.2) 1.6 μL+CVP base 2.5 μL]]/dose low dose group: [vaccine 0.033 μL+Ampligen 0.26 μL+M/75 PBS (PH 7.2) 2.207 μL+CVP base 2.5 μL]/dose The vaccine for non-addition transnasal administration used as a negative control was obtained by removing Ampligen and CVP base from the above-mentioned composition, and adding M/75 PBS (pH 7.2) in a volume corresponding thereto. In addition, the vaccine for non-addition intramuscular administration was [vaccine 0.3 μL+M/75 PBS (pH 7.2) 49.7 μL]/dose.

Vaccine administration volume: (Table 11)

The transnasal administration group was administered with 6 μL into one nostril, and the control non-addition vaccine subcutaneous administration group was administered with 50 μL to unilateral femoral area.

6. Measurement items (Tables 12-19)

nasal swab: specific IgA-ELISA antibody titer and cross-reactive IgA-ELISA antibody titer:

serum specific IgG-ELISA antibody titer, specific HI (hemagglutination inhibition) antibody titer and cross-reactive HI antibody titer, specific neutralizing antibody titer and cross-reactive neutralizing antibody titer were measured. Among the above-mentioned measurement items, the outline of the measurement method of the ELISA antibody titer was as described below.

Vaccine antigen (diluted with 100 mM carbonate buffer (pH 9.6) to protein concentration of 1 μg/mL) was solid phased (4° C., overnight) on a 96-well ELISA plate at 100 μL/well, and washed 3 times with PBS containing 0.1% Tween 20. A sample diluted 2-fold series or negative control was added at 100 μL/well. Then, the plate was incubated at 37° C. for 1 hr, and washed 3 times with PBS containing 0.1% Tween 20. An antibody for detection (alkaliphosphatase-labeled anti-mouse IgG or biotin-labeled anti-mouse IgA) was added at 100 μL/well. The plate was incubated at 37° C. for 1 hr, and washed 3 times with PBS containing 0.1% Tween 20 (for IgA detection, alkaliphosphatase-labeled streptavidin was added at 100 μL/well, incubated at 37° C. for 1 hr, and washed 3 times with PBS containing 0.1% Tween 20). Then, 4-nitrophenylphosphate (1 mg/mL, diluted with 0.1 M diethanolamine (pH 9.8)) was added at 100 μL/well, and the plate was shaded. After incubation at room temperature for 30 min, the absorbance at 405 nm was measured.

The maximum dilution rate that affords an absorbance of sample exceeding the average absorbance of negative control+2SD was taken as the antibody titer of the sample. For specific antibody titer, the same strain as the administration vaccine antigen was used and, for cross-reactive antibody titer, vaccine antigen of a different strain was used. In the following, HI•neutralizing antibody titer were measured in the same manner. specific HI (hemagglutination inhibition) antibody titer and cross-reactive HI antibody titer:

The test was performed according to the description in the "pathogen detection manual" (edited by National Institute of infectious Diseases). The red blood cells used were derived from chicken.

specific neutralizing antibody titer and cross-reactive neutralizing antibody titer:

The test was performed according to the description in the "pathogen detection manual" (edited by National Institute of infectious Diseases). The culture after virus infection was performed for 4 days. In addition, a method comprising staining the cells with 0.1% Naphtol Blue Black/0.1% sodium acetate/9% acetic acid, drying the cell culture plate, adding 0.1 M sodium hydroxide and measuring the absorbance at 630 nm was used for distinction between virus infectious cells and non-infectious cells.

(Results)

Figure 3:
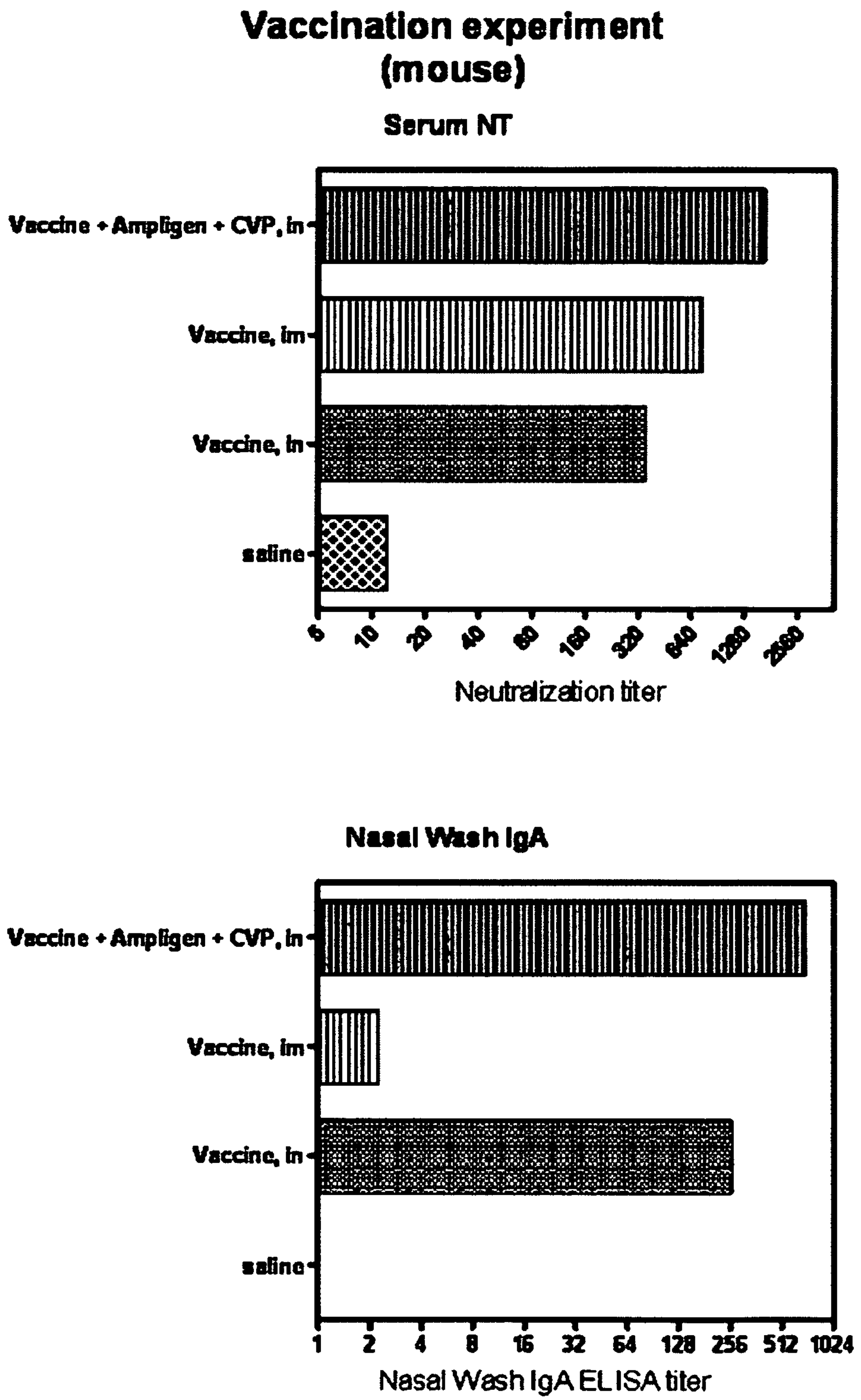
FIG. 3 is a summary of the vaccine administration test in Example 2.

BALB/c mice (♀, 6.5 w when test was started) were used, and immune response was examined when the antigen (A/Indonesia/5/2005 (H5N1)) supplemented with ampligen at 20-fold ratio of HA antigen, and CVP was transnasally administered 1-4 times, using, as a comparison control, an antigen+Ampligen+CVP transnasal administration group for the first half of the test group and transnasal administration of antigen alone/intramuscular administration of antigen alone/saline transnasal administration for the latter half. The results are shown in Tables 12-19 and FIG. 3.

In the antigen+Ampligen+CVP group, several to dozen-fold mucous membrane IgA/serum IgG and NT antibody titer were observed as compared to the antigen alone transnasal administration group, and the difference was remarkable in the groups with lower dose and less administration frequency.

Conventional common knowledge holds that, as compared to vaccines for subcutaneous or intramuscular administration, transnasal administration-type vaccines show lower specific neutralizing antibody, serum specific IgG antibody titer and HI antibody titer. However, the vaccine evaluated at this time was found to acquire specific neutralizing antibody, serum specific IgG antibody titer and HI antibody titer equivalent to or above those of the vaccines with conventional composition and administration method, by the addition of Ampligen® and the like.

Furthermore, the immune response of the samples obtained by this test with the same strain as the administered antigen and a strain with different antigenicity was examined to confirm cross-reactivity.

TABLE 10

New type Influ A/Indo Ampligen.CVP addition vaccine consideration of dose.administration frequency in mouse; Serum NT test (2009 Aug. 24, Aug. 27) cross-reaction (A/VN)

| | | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| antigen amount of administration (μg HA/dose) | | 0.3 | 0.1 | 0.033 | 0.3 | 0.1 | 0.033 | 0.3 | 0.1 | 0.033 | 0.3 | 0.1 | 0.033 | 0.3 | 0.1 | 0.033 |
| administration frequency | | | 4 | | | 3 | | | 2 | | | 1 | | | 4 | |
| administration route | | trans-nasal | trans-nasal | trans-nasal | trans-nasal | trans-nasal | trans-nasal | trans-nasal | trans-nasal | trans-nasal | trans-nasal | trans-nasal | trans-nasal | trans-nasal | trans-nasal | trans-nasal |
| adjuvant (Ampligen), CVP addition | | yes | yes | yes | yes | yes | yes | yes | yes | yes | yes | yes | yes | none | none | none |
| animal No. | 1 | 40 | 20 | 10 | 40 | 160 | 40 | 5 | 40 | 40 | 80 | 80 | 40 | 10 | 40 | 10 |
| | 2 | 20 | 40 | 40 | 80 | 20 | 80 | 10 | 80 | 20 | 80 | 80 | 40 | 40 | 5 | 20 |
| | 3 | 40 | 40 | 10 | 40 | 40 | 160 | 20 | 80 | 20 | 80 | 40 | 20 | 40 | 20 | 20 |
| | 4 | 160 | 40 | 80 | 40 | 10 | 40 | 10 | 40 | 40 | 80 | 40 | 40 | 10 | 80 | 10 |
| | 5 | 80 | 20 | 20 | 40 | 80 | 40 | 40 | 10 | 40 | 80 | 40 | 40 | 10 | 20 | 20 |
| | 6 | 10 | 80 | 10 | 20 | 40 | 20 | 20 | 40 | 40 | 80 | 20 | 10 | 10 | 20 | 20 |
| | 7 | 20 | 10 | 10 | 40 | 40 | 80 | 40 | 40 | 40 | 80 | 10 | 40 | 10 | 20 | 5 |
| | 8 | 40 | 10 | 20 | 80 | 40 | 40 | 10 | 40 | 40 | 80 | 40 | 5 | 20 | 20 | 10 |
| | 9 | 40 | | 20 | 40 | 80 | 20 | 80 | 40 | 40 | 80 | 40 | 5 | 20 | 20 | 5 |
| | 10 | 20 | | 80 | 80 | | | | | 80 | 80 | 40 | 40 | 40 | 20 | 20 |
| average antibody titer (GMT) | | 34.8 | 25.9 | 21.4 | 45.9 | 43.2 | 46.7 | 18.5 | 40.0 | 37.3 | 80.0 | 37.3 | 21.4 | 17.4 | 21.4 | 12.3 |
| variance | | 44.2 | 23.1 | 27.9 | 21.6 | 45.3 | 44.1 | 24.0 | 21.9 | 16.3 | 0.0 | 22.1 | 16.0 | 13.7 | 20.6 | 6.6 |

| | | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|
| antigen amount of administration (μg HA/dose) | | 0.3 | 0.1 | 0.033 | 0.3 | 0.1 | 0.033 | 0.3 | 0.1 | 0.033 | 0.3 | 0.3 | 0.3 | 0.3 | none (saline) |
| administration frequency | | | 3 | | | 2 | | | 1 | | 4 | 3 | 2 | 1 | 1 |
| administration route | | trans-nasal | trans-nasal | trans-nasal | trans-nasal | trans-nasal | trans-nasal | trans-nasal | trans-nasal | trans-nasal | intra-mus-cular | intra-muscular | intra-mus-cular | intra-muscular | trans-nasal |
| adjuvant (Ampligen), CVP addition | | none | none | none | none | none | none | none | none | none | none | none | none | none | none |
| animal No. | 1 | 40 | 40 | 40 | 20 | 40 | 40 | 40 | 20 | 40 | 80 | 20 | 80 | 80 | 40 |
| | 2 | 40 | 40 | 40 | 40 | 20 | 40 | 20 | 40 | 40 | 20 | 40 | 80 | 40 | 80 |
| | 3 | 40 | 20 | 40 | 20 | 40 | 20 | 40 | 40 | 40 | 80 | 40 | 80 | 40 | 40 |
| | 4 | 20 | 40 | 40 | 40 | 5 | 40 | 40 | 80 | 40 | 80 | 160 | 40 | 5 | 10 |
| | 5 | 80 | 40 | 40 | 40 | 40 | 40 | 20 | 20 | 40 | 20 | 80 | 40 | 40 | 5 |
| | 6 | 80 | 20 | 40 | 20 | 40 | 20 | 20 | 40 | 40 | 40 | 80 | 40 | 40 | 5 |
| | 7 | 40 | 40 | 40 | 20 | 40 | 20 | 40 | 20 | 40 | 40 | 40 | 40 | 40 | 20 |
| | 8 | 20 | 20 | 40 | 20 | 10 | 20 | 40 | 40 | 40 | 160 | 80 | 40 | 10 | 40 |
| | 9 | 20 | 40 | 40 | 40 | 40 | 20 | 20 | 20 | 20 | 20 | 80 | 40 | 80 | 20 |
| | 10 | 80 | | 40 | 5 | 40 | 40 | 40 | 40 | 10 | 20 | 80 | 40 | 40 | 20 |
| average antibody titer (GMT) | | 40.0 | 31.7 | 40.0 | 23.0 | 26.4 | 28.3 | 30.3 | 32.5 | 32.5 | 42.9 | 60.6 | 40.0 | 32.5 | 20.0 |
| variance | | 25.0 | 10.0 | 0.0 | 12.5 | 14.2 | 10.5 | 10.3 | 18.4 | 10.8 | 45.0 | 39.2 | 19.3 | 24.3 | 22.9 |

TABLE 11

Vaccine composition

| dose | admini-stration group | vaccine stock solution (μL) | Ampligen (μL) | CVP (μL) | M/75 PBS (pH 7.2) (μL) | total (mL) | note |
|---|---|---|---|---|---|---|---|
| high dose (0.3 μg HA/dose) | 1, 4, 7, 10 | 302.42 | 2400.0 | 3000 | 297.58 | 6 | for 1000 times (transnasal) |
| moderate dose (0.1 μg HA/dose) | 2, 5, 8, 11 | 100.81 | 800.0 | 3000 | 2099.19 | 6 | for 1000 times (transnasal) |
| low dose (0.033 μg HA/dose) | 3, 6, 9, 12 | 33.27 | 264.0 | 3000 | 2702.73 | 6 | for 1000 times (transnasal) |
| high dose (0.3 μg HA/dose) | 13, 16, 19, 22 | 302.42 | | | 5697.58 | 6 | for 1000 times (transnasal) |

TABLE 11-continued

| Vaccine composition | | | | | | | |
|---|---|---|---|---|---|---|---|
| dose | admini-stration group | vaccine stock solution (μL) | Ampligen (μL) | CVP (μL) | M/75 PBS (pH 7.2) (μL) | total (mL) | note |
| moderate dose (0.1 μg HA/dose) | 14, 17, 20, 23 | 100.81 | | | 5899.19 | 6 | for 1000 times (transnasal) |
| low dose (0.033 μg HA/dose) | 15, 18, 21, 24 | 33.27 | | | 5966.73 | 6 | for 1000 times (transnasal) |
| high dose (0.3 μg HA/dose) | 25, 26, 27, 28 | 30.24 | | | 4969.76 | 5 | for 100 times (muscular injection) |
| saline | 29 | | | | 600 (saline) | | for 100 times (transnasal) |

Whole particles influenza vaccine: A/Indo/5/2005(H5N1) lot No.; FPBMW0612-c (protein concentration: 3110 μg/mL, HA content 992 μg HA/mL)

Ampligen (manufactured by Hemispherx): lot; 0701HE (containing 2.5 mg/mL Ampligen)

CVP base (manufactured by Toko Yakuhin Kogyo Kabushiki Kaisya): lot INF-N28; carboxyvinyl polymer 1.1%, L-arginine 2.4%, glycerol 2%

TABLE 12

New type Influ A/Indo Ampligen · CVP addition vaccine consideration of mouse dose · administration frequency; Nasal wash IgA-ELISA test (2009 Jun. 19/Jul. 7)

| | | group | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| antigen amount of administration (μg HA/dose) | | 0.3 | 0.1 | 0.033 | 0.3 | 0.1 | 0.033 | 0.3 | 0.1 | 0.033 | 0.3 | 0.1 | 0.033 | 0.3 | 0.1 | 0.033 |
| administration frequency | | 4 | | | | 3 | | | 2 | | | 1 | | | 4 | |
| administration route | | trans-nasal | trans-nasal | trans-nasal | trans-nasal | trans-nasal | trans-nasal | trans-nasal | trans-nasal | trans-nasal | trans-nasal | trans-nasal | trans-nasal | trans-nasal | trans-nasal | trans-nasal |
| adjuvant (Ampligen), CVP addition | | yes | yes | yes | yes | yes | yes | yes | yes | yes | yes | yes | yes | none | none | none |
| animal No. | 1 | 512 | 512 | 512 | 256 | 512 | 128 | 1024 | 512 | 512 | 128 | 1 | 8 | 512 | 512 | 128 |
| | 2 | 512 | 512 | 512 | 256 | 512 | 512 | 4096 | 512 | 256 | 128 | 64 | 2 | 256 | 1024 | 64 |
| | 3 | 512 | 1024 | 256 | 256 | 512 | 512 | 4096 | 1024 | 512 | 128 | 4 | 4 | 512 | 128 | 128 |
| | 4 | 512 | 512 | 512 | 2048 | 512 | 512 | 2048 | 1024 | 128 | 128 | 16 | 4 | 512 | 512 | 64 |
| | 5 | 512 | 512 | 512 | 512 | 512 | 512 | 1024 | 1024 | 256 | 256 | 64 | 4 | 256 | 128 | 64 |
| | 6 | 512 | 512 | 1024 | 1024 | 512 | 128 | 2048 | 512 | 512 | 32 | 1 | 64 | 512 | 512 | 64 |
| | 7 | 512 | 1024 | 512 | 128 | 512 | 512 | 2048 | 512 | 1024 | 128 | 8 | 4 | 256 | 128 | 64 |
| | 8 | 512 | 512 | 512 | 1024 | 512 | 512 | 512 | 128 | 256 | 32 | 32 | 2 | 256 | 128 | 64 |
| | 9 | 512 | | 512 | 1024 | 512 | 512 | 2048 | 128 | 512 | 64 | 1 | 4 | 512 | 128 | 128 |
| | 10 | 512 | | 512 | 512 | | | | | 512 | 128 | 2 | 4 | 512 | 64 | 64 |
| average antibody titer (GMT) | | 512.0 | 608.9 | 512.0 | 512.0 | 512.0 | 376.3 | 1755.6 | 474.0 | 388.0 | 97.0 | 6.5 | 4.9 | 388.0 | 222.9 | 78.8 |
| variance | | 0.0 | 237.0 | 188.9 | 588.9 | 0.0 | 169.3 | 1265.7 | 356.3 | 250.6 | 64.4 | 25.5 | 19.0 | 132.2 | 308.3 | 30.9 |
| positive conversion ratio (antibody titer not less than 32, %) | | 100.0 | 100.0 | 100.0 | 100.0 | 90.0 | 90.0 | 100.0 | 100.0 | 100.0 | 100.0 | 30.0 | 10.0 | 100.0 | 100.0 | 100.0 |

| | group | | | | | | | | | | | | | |
|---|---|---|---|---|---|---|---|---|---|---|---|---|---|---|
| | 16 | 17 | 18 | 19 | 20 | 21 | 22 | 23 | 24 | 25 | 26 | 27 | 28 | 29 |
| antigen amount of administration (μg HA/dose) | 0.3 | 0.1 | 0.033 | 0.3 | 0.1 | 0.033 | 0.3 | 0.1 | 0.033 | 0.3 | 0.3 | 0.3 | 0.3 | none (saline) |
| administration frequency | | 3 | | | 2 | | | 1 | | 4 | 3 | 2 | 1 | 1 |
| administration route | trans-nasal | trans-nasal | trans-nasal | trans-nasal | trans-nasal | trans-nasal | trans-nasal | trans-nasal | trans-nasal | intra-muscular | intra-muscular | intra-muscular | intra-muscular | trans-nasal |
| adjuvant (Ampligen), CVP addition | none | none | none | none | none | none | none | none | none | none | none | none | none | none |

TABLE 12-continued

| | | | | | | | | | | | | | | | |
|---|---|---|---|---|---|---|---|---|---|---|---|---|---|---|---|
| animal No. | 1 | 256 | 64 | 64 | 1024 | 256 | 256 | 64 | 1 | 2 | 8 | 2 | 1 | 1 | 1 |
| | 2 | 128 | 64 | 128 | 256 | 128 | 32 | 32 | 2 | 2 | 2 | 2 | 2 | 1 | 1 |
| | 3 | 128 | 32 | 256 | 512 | 16 | 32 | 32 | 2 | 2 | 2 | 2 | 2 | 1 | 1 |
| | 4 | 512 | 64 | 64 | 1024 | 128 | 8 | 32 | 2 | 2 | 2 | 2 | 1 | 1 | 1 |
| | 5 | 512 | 64 | 32 | 512 | 128 | 32 | 8 | 1 | 2 | 2 | 2 | 1 | 1 | 1 |
| | 6 | 256 | 128 | 64 | 512 | 64 | 16 | 8 | 8 | 4 | 1 | 2 | 2 | 1 | 1 |
| | 7 | 128 | 64 | 64 | 64 | 16 | 128 | 64 | 4 | 4 | 2 | 4 | 1 | 1 | 1 |
| | 8 | 256 | 32 | 64 | 256 | 16 | 16 | 8 | 4 | 4 | 2 | 2 | 2 | 1 | 1 |
| | 9 | 128 | 64 | 64 | 512 | 32 | 16 | 8 | 8 | 2 | 2 | 2 | 1 | 1 | 1 |
| | 10 | 256 | | 32 | 32 | 32 | 16 | 32 | 4 | 4 | 2 | 2 | 1 | 1 | 1 |
| average antibody titer (GMT) | | 222.9 | 59.3 | 68.6 | 315.2 | 52.0 | 29.9 | 21.1 | 2.8 | 2.6 | 2.1 | 2.1 | 1.3 | 1.0 | 1.0 |
| variance | | 147.8 | 27.7 | 66.1 | 344.7 | 78.2 | 78.6 | 21.7 | 2.6 | 1.0 | 2.0 | 0.6 | 0.5 | 0.0 | 0.0 |
| positive conversion ratio (antibody titer not less than 32, %) | | 100.0 | 100.0 | 100.0 | 100.0 | 70.0 | 50.0 | 60.0 | 0.0 | 0.0 | 0.0 | 0.0 | 0.0 | 0.0 | 0.0 |

TABLE 13

New type Influ A/Indo Ampligen.CVP addition vaccine consideration of mouse dose.administration frequency; Serum IgG-ELISA test (2009 Jul. 7)

| | | group | | | | | | | | |
|---|---|---|---|---|---|---|---|---|---|---|
| | | 1 | 2 | 3 | 4 | 5 | 6 | 7 | 8 | 9 |
| antigen amount of administration (μg HA/dose) | | 0.3 | 0.1 | 0.033 | 0.3 | 0.1 | 0.033 | 0.3 | 0.1 | 0.033 |
| administration frequency | | | 4 | | | 3 | | | 2 | |
| administration route | | trans-nasal | trans-nasal | trans-nasal | trans-nasal | trans-nasal | trans-nasal | trans-nasal | trans-nasal | trans-nasal |
| adjuvant (Ampligen), CVP addition | | yes | yes | yes | yes | yes | yes | yes | yes | yes |
| animal No. | 1 | 51200 | 102400 | 12800 | 51200 | 25600 | 25600 | 12800 | 12800 | 3200 |
| | 2 | 102400 | 102400 | 25600 | 25600 | 51200 | 6400 | 12800 | 3200 | 6400 |
| | 3 | 102400 | 12800 | 25600 | 51200 | 25600 | 1600 | 12800 | 1600 | 3200 |
| | 4 | 204800 | 12800 | 25600 | 51200 | 25600 | 3200 | 12800 | 12800 | 3200 |
| | 5 | 12800 | 25600 | 12800 | 25600 | 51200 | 6400 | 6400 | 3200 | 1600 |
| | 6 | 25600 | 51200 | 51200 | 51200 | 25600 | 6400 | 6400 | 12800 | 3200 |
| | 7 | 25600 | 25600 | 12800 | 51200 | 51200 | 3200 | 25600 | 12800 | 6400 |
| | 8 | 102400 | 25600 | 25600 | 25600 | 25600 | 25600 | 12800 | 3200 | 12800 |
| | 9 | 102400 | | 102400 | 51200 | 51200 | 25600 | 6400 | 3200 | 6400 |
| | 10 | 25600 | | 51200 | 25600 | | | | | 6400 |
| average antibody titer (GMT) | | 54874.8 | 33199.1 | 27437.4 | 38802.3 | 34836.2 | 7465.8 | 10972.7 | 5486.4 | 4525.5 |
| variance | | 59259.1 | 37474.6 | 27684.1 | 13219.8 | 13492.4 | 10666.7 | 5938.9 | 5252.7 | 3204.4 |

| | | group | | | | | | | | |
|---|---|---|---|---|---|---|---|---|---|---|
| | | 10 | 11 | 12 | 13 | 14 | 15 | 16 | 17 | 18 |
| antigen amount of administration (μg HA/dose) | | 0.3 | 0.1 | 0.033 | 0.3 | 0.1 | 0.033 | 0.3 | 0.1 | 0.033 |
| administration frequency | | | 1 | | | 4 | | | 3 | |
| administration route | | trans-nasal | trans-nasal | trans-nasal | trans-nasal | trans-nasal | trans-nasal | trans-nasal | trans-nasal | trans-nasal |
| adjuvant (Ampligen), CVP addition | | yes | yes | yes | none | none | none | none | none | none |
| animal No. | 1 | 800 | 3200 | 200 | 6400 | 6400 | 3200 | 6400 | 1600 | 800 |
| | 2 | 400 | 3200 | 100 | 6400 | 6400 | 1600 | 3200 | 3200 | 3200 |
| | 3 | 400 | 200 | 400 | 3200 | 6400 | 3200 | 12800 | 3200 | 12800 |
| | 4 | 1600 | 200 | 200 | 3200 | 25600 | 6400 | 12800 | 3200 | 1600 |
| | 5 | 1600 | 200 | 400 | 6400 | 12800 | 1600 | 6400 | 1600 | 1600 |
| | 6 | 1600 | 1600 | 400 | 6400 | 25600 | 1600 | 6400 | 800 | 12800 |
| | 7 | 400 | 200 | 100 | 25600 | 3200 | 1600 | 6400 | 1600 | 1600 |
| | 8 | 6400 | 6400 | 100 | 6400 | 3200 | 1600 | 12800 | 12800 | 3200 |
| | 9 | 200 | 200 | 400 | 25600 | 25600 | 1600 | 6400 | 3200 | 1600 |
| | 10 | 400 | 3200 | 1600 | 12800 | 1600 | 1600 | 12800 | | 800 |
| average antibody titer (GMT) | | 800.0 | 800.0 | 263.9 | 7879.3 | 7879.3 | 2111.2 | 7879.3 | 2539.8 | 2425.1 |
| variance | | 1853.4 | 2104.1 | 445.8 | 8506.6 | 10064.3 | 1554.9 | 3710.4 | 3622.2 | 4710.3 |

TABLE 13-continued

New type Influ A/Indo Ampligen.CVP addition vaccine consideration of mouse dose.administration frequency; Serum IgG-ELISA test (2009 Jul. 7)

| | | group | | | | | | | | | | |
|---|---|---|---|---|---|---|---|---|---|---|---|---|
| | | 19 | 20 | 21 | 22 | 23 | 24 | 25 | 26 | 27 | 28 | 29 |
| antigen amount of administration (μg HA/dose) | | 0.3 | 0.1 | 0.033 | 0.3 | 0.1 | 0.033 | 0.3 | 0.3 | 0.3 | 0.3 | none (saline) |
| administration frequency | | | 2 | | | 1 | | 4 | 3 | 2 | 1 | 1 |
| administration route | | trans-nasal | trans-nasal | trans-nasal | trans-nasal | trans-nasal | trans-nasal | intra-muscular | intra-muscular | intra-muscular | intra-mus-cular | trans-nasal |
| adjuvant (Ampligen), CVP addition | | none | none | none | none | none | none | none | none | none | none | none |
| animal No. | 1 | 1600 | 1600 | 1600 | 200 | 50 | 50 | 25600 | 51200 | 3200 | 1600 | 50 |
| | 2 | 3200 | 1600 | 100 | 200 | 100 | 50 | 12800 | 51200 | 6400 | 400 | 50 |
| | 3 | 3200 | 200 | 400 | 100 | 100 | 50 | 25600 | 51200 | 12800 | 200 | 50 |
| | 4 | 12800 | 400 | 100 | 200 | 100 | 50 | 12800 | 51200 | 12800 | 400 | 50 |
| | 5 | 12800 | 800 | 400 | 200 | 100 | 50 | 12800 | 204800 | 6400 | 400 | 50 |
| | 6 | 1600 | 400 | 200 | 200 | 100 | 50 | 25600 | 51200 | 12800 | 200 | 50 |
| | 7 | 800 | 100 | 1600 | 200 | 50 | 50 | 25600 | 102400 | 12800 | 400 | 50 |
| | 8 | 3200 | 200 | 100 | 100 | 100 | 50 | 12800 | 102400 | 12800 | 400 | 50 |
| | 9 | 3200 | 200 | 100 | 100 | 100 | 50 | 25600 | 102400 | 25600 | 200 | 50 |
| | 10 | 3200 | 200 | 100 | 200 | 100 | 50 | 102400 | 102400 | 12800 | 1600 | 50 |
| average antibody titer (GMT) | | 3200.0 | 373.2 | 246.2 | 162.5 | 87.1 | 50.0 | 22286.1 | 77604.7 | 10396.8 | 428.7 | 50.0 |
| variance | | 4431.0 | 577.4 | 607.5 | 48.3 | 21.1 | 0.0 | 26849.5 | 48572.6 | 6043.4 | 545.3 | 0.0 |

TABLE 14

New type Influ A/Indo Ampligen.CVP addition vaccine consideration of mouse dose.administration frequency; Serum HI test (2009 Jun. 19)

| | | group | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| antigen amount of administration (μg HA/dose) | | 0.3 | 0.1 | 0.033 | 0.3 | 0.1 | 0.033 | 0.3 | 0.1 | 0.033 | 0.3 | 0.1 | 0.033 | 0.3 | 0.1 | 0.033 |
| administration frequency | | 4 | | | | 3 | | | 2 | | | 1 | | | 4 | |
| administration route | | trans-nasal | trans-nasal | trans-nasal | trans-nasal | trans-nasal | trans-nasal | trans-nasal | trans-nasal | trans-nasal | trans-nasal | trans-nasal | trans-nasal | trans-nasal | trans-nasal | trans-nasal |
| adjuvant (Ampligen), CVP addition | | yes | yes | yes | yes | yes | yes | yes | yes | yes | yes | yes | yes | none | none | none |
| animal No. | 1 | 20 | 5 | 20 | 40 | 20 | 10 | 40 | 20 | 5 | 5 | 10 | 5 | 5 | 5 | 5 |
| | 2 | 5 | 160 | 40 | 20 | 20 | 10 | 5 | 10 | 5 | 5 | 10 | 5 | 5 | 5 | 5 |
| | 3 | 40 | 40 | 10 | 40 | 5 | 5 | 20 | 10 | 5 | 5 | 5 | 10 | 5 | 5 | 5 |
| | 4 | 80 | 10 | 10 | 20 | 10 | 5 | 10 | 40 | 5 | 5 | 5 | 10 | 5 | 5 | 5 |
| | 5 | 20 | 10 | 20 | 40 | 20 | 5 | 5 | 5 | 5 | 10 | 5 | 5 | 5 | 5 | 5 |
| | 6 | 20 | 40 | 5 | 80 | 20 | 5 | 10 | 20 | 5 | 10 | 5 | 5 | 5 | 5 | 5 |
| | 7 | 20 | 5 | 10 | 20 | 20 | 5 | 80 | 20 | 10 | 5 | 5 | 5 | 5 | 5 | 5 |
| | 8 | 40 | 20 | 20 | 5 | 20 | 5 | 40 | 10 | 80 | 20 | 10 | 5 | 5 | 5 | 5 |
| | 9 | 40 | | 10 | 20 | 40 | 10 | 40 | 10 | 20 | 5 | 5 | 5 | 10 | 5 | 5 |
| | 10 | 20 | | 40 | 10 | | | | | 5 | 5 | 10 | 5 | 5 | 5 | 5 |
| average antibody titer (GMT) | | 24.6 | 18.3 | 15.2 | 23.0 | 17.1 | 6.3 | 18.5 | 13.6 | 8.1 | 6.6 | 6.6 | 5.7 | 5.4 | 5.0 | 5.0 |
| variance | | 20.9 | 52.0 | 12.5 | 21.7 | 9.5 | 2.5 | 24.8 | 10.5 | 23.5 | 4.9 | 2.6 | 2.1 | 1.6 | 0.0 | 0.0 |
| seroconversion rate (antibody titer not less than 40, %) | | 40.0 | 37.5 | 20.0 | 40.0 | 11.1 | 0.0 | 44.4 | 11.1 | 10.0 | 0.0 | 0.0 | 0.0 | 0.0 | 0.0 | 0.0 |

TABLE 14-continued

New type Influ A/Indo Ampligen.CVP addition vaccine consideration of mouse dose.administration frequency; Serum HI test (2009 Jun. 19)

| | | group | | | | | | | | | | | | | |
|---|---|---|---|---|---|---|---|---|---|---|---|---|---|---|---|
| | | 16 | 17 | 18 | 19 | 20 | 21 | 22 | 23 | 24 | 25 | 26 | 27 | 28 | 29 |
| antigen amount of administration (μg HA/dose) | | 0.3 | 0.1 | 0.033 | 0.3 | 0.1 | 0.033 | 0.3 | 0.1 | 0.033 | 0.3 | 0.3 | 0.3 | 0.3 | none (saline) |
| administration frequency | | | 3 | | | 2 | | | 1 | | 4 | 3 | 2 | 1 | 1 |
| administration route | | trans-nasal | trans-nasal | trans-nasal | trans-nasal | trans-nasal | trans-nasal | trans-nasal | trans-nasal | trans-nasal | intra-mus-cular | intra-muscular | intra-mus-cular | intra-muscular | trans-nasal |
| adjuvant (Ampligen), CVP addition | | none | none | none | none | none | none | none | none | none | none | none | none | none | none |
| animal No. | 1 | 5 | 5 | 5 | 5 | 5 | 10 | 5 | 5 | 5 | 20 | 40 | 5 | 10 | 5 |
| | 2 | 5 | 10 | 5 | 5 | 5 | 5 | 5 | 5 | 5 | 20 | 20 | 5 | 5 | 5 |
| | 3 | 20 | 5 | 5 | 5 | 5 | 5 | 5 | 5 | 5 | 10 | 20 | 20 | 10 | 5 |
| | 4 | 5 | 5 | 5 | 10 | 5 | 5 | 5 | 5 | 5 | 10 | 40 | 10 | 5 | 5 |
| | 5 | 5 | 5 | 5 | 5 | 5 | 5 | 5 | 5 | 5 | 5 | 160 | 5 | 5 | 5 |
| | 6 | 10 | 5 | 5 | 5 | 5 | 5 | 5 | 5 | 5 | 5 | 40 | 5 | 5 | 5 |
| | 7 | 5 | 5 | 5 | 5 | 5 | 5 | 5 | 5 | 5 | 10 | 40 | 10 | 5 | 5 |
| | 8 | 5 | 5 | 5 | 5 | 5 | 5 | 5 | 5 | 5 | 10 | 160 | 10 | 5 | 5 |
| | 9 | 5 | 5 | 5 | 5 | 5 | 5 | 5 | 5 | 5 | 20 | 80 | 20 | 5 | 5 |
| | 10 | 20 | | 5 | 5 | 5 | 5 | 5 | 5 | 5 | 10 | 40 | 20 | 10 | 5 |
| average antibody titer (GMT) | | 7.1 | 5.4 | 5.0 | 5.4 | 5.0 | 5.4 | 5.0 | 5.0 | 5.0 | 10.7 | 49.2 | 9.3 | 6.2 | 5.0 |
| variance | | 6.3 | 1.7 | 0.0 | 1.6 | 0.0 | 1.6 | 0.0 | 0.0 | 0.0 | 5.9 | 53.2 | 6.6 | 2.4 | 0.0 |
| seroconversion rate (antibody titer not less than 40, %) | | 0.0 | 0.0 | 0.0 | 0.0 | 0.0 | 0.0 | 0.0 | 0.0 | 0.0 | 0.0 | 80.0 | 0.0 | 0.0 | 0.0 |

TABLE 15

Serum HI test (2009 Jul. 23) cross-reaction (A/VN)

| | | group | | | | | |
|---|---|---|---|---|---|---|---|
| | | 4 | 5 | 7 | 8 | 26 | 27 |
| antigen amount of administration (μg HA/dose) | | 0.3 | 0.1 | 0.3 | 0.1 | 0.3 | 0.3 |
| administration frequency | | 3 | | 2 | | 3 | 2 |
| administration route | | trans-nasal | trans-nasal | trans-nasal | trans-nasal | intra-muscular | intra-muscular |
| adjuvant (Ampligen), CVP addition | | yes | yes | yes | yes | none | none |
| animal No. | 1 | 5 | 20 | 5 | 5 | 5 | 5 |
| | 2 | 5 | 5 | 5 | 5 | 5 | 5 |
| | 3 | 5 | 5 | 5 | 5 | 20 | 5 |
| | 4 | 5 | 5 | 5 | 5 | 10 | 5 |
| | 5 | 5 | 10 | 5 | 5 | 5 | 5 |
| | 6 | 5 | 5 | 5 | 5 | 5 | 5 |
| | 7 | 5 | 20 | 5 | 5 | 5 | 5 |
| | 8 | 5 | 20 | 5 | 5 | 5 | 5 |
| | 9 | 5 | 5 | 5 | 10 | 5 | 5 |
| | 10 | 5 | | | | 5 | 5 |
| average antibody titer (GMT) | | 5.0 | 8.6 | 5.0 | 5.4 | 6.2 | 5.0 |
| variance | | 0.0 | 7.3 | 0.0 | 1.7 | 4.8 | 0.0 |
| seroconversion rate (antibody titer not less than 40, %) | | 0.0 | 0.0 | 0.0 | 0.0 | 0.0 | 0.0 |

TABLE 16

New type Influ A/Indo Ampligen.CVP addition vaccine consideration of mouse dose.administration frequency; Serum NT test (2009 Jul. 27, Aug 3)

| | group | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| antigen amount of administration (μg HA/dose) | 0.3 | 0.1 | 0.033 | 0.3 | 0.1 | 0.033 | 0.3 | 0.1 | 0.033 | 0.3 | 0.1 | 0.033 | 0.3 | 0.1 | 0.033 |

TABLE 16-continued

New type Influ A/Indo Ampligen.CVP addition vaccine consideration of mouse dose.administration frequency; Serum NT test (2009 Jul. 27, Aug 3)

| | | | | | | | | | | | | | | | | |
|---|---|---|---|---|---|---|---|---|---|---|---|---|---|---|---|---|
| administration frequency | | | 4 | | | 3 | | | 2 | | | 1 | | | 4 | |
| administration route | | trans-nasal | trans-nasal | trans-nasal | trans-nasal | trans-nasal | trans-nasal | trans-nasal | trans-nasal | trans-nasal | trans-nasal | trans-nasal | trans-nasal | trans-nasal | trans-nasal | trans-nasal |
| adjuvant (Ampligen), CVP addition | | yes | yes | yes | yes | yes | yes | yes | yes | yes | yes | yes | yes | none | none | none |
| animal No. | 1 | 1280 | 5120 | 640 | 2560 | 160 | 320 | 640 | 640 | 80 | 80 | 160 | 40 | 320 | 320 | 80 |
| | 2 | 80 | 5120 | 1280 | 640 | 640 | 320 | 640 | 160 | 320 | 80 | 320 | 40 | 1280 | 80 | 40 |
| | 3 | 2560 | 1280 | 320 | 2560 | 320 | 80 | 640 | 320 | 160 | 80 | 40 | 80 | 640 | 80 | 40 |
| | 4 | 2560 | 320 | 640 | 1280 | 320 | 80 | 640 | 640 | 80 | 80 | 40 | 80 | 1280 | 640 | 80 |
| | 5 | 320 | 320 | 320 | 2560 | 640 | 640 | 320 | 320 | 80 | 80 | 40 | 80 | 1280 | 160 | 20 |
| | 6 | 640 | 2560 | 640 | 5120 | 640 | 80 | 160 | 320 | 160 | 160 | 20 | 10 | 320 | 320 | 20 |
| | 7 | 1280 | 640 | 320 | 640 | 640 | 80 | 640 | 640 | 160 | 80 | 5 | 40 | 320 | 160 | 20 |
| | 8 | 1280 | 640 | 2560 | 160 | 640 | 640 | 320 | 320 | 640 | 320 | 320 | 5 | 80 | 80 | 20 |
| | 9 | 2560 | | 320 | 640 | 1280 | 320 | 640 | 320 | 160 | 40 | 40 | 5 | 640 | 640 | 10 |
| | 10 | 640 | | 2560 | 320 | | | | | 160 | 80 | 160 | 40 | 160 | 10 | 20 |
| average antibody titer (GMT) | | 905.1 | 1173.8 | 685.9 | 1039.7 | 508.0 | 201.6 | 470.3 | 373.3 | 160.0 | 91.9 | 60.6 | 28.3 | 452.5 | 149.3 | 28.3 |
| variance | | 947.5 | 2057.9 | 892.4 | 1553.2 | 320.0 | 230.2 | 192.3 | 180.9 | 169.7 | 80.1 | 121.0 | 30.0 | 480.7 | 229.6 | 25.5 |

| | | group | | | | | | | | | | | | | |
|---|---|---|---|---|---|---|---|---|---|---|---|---|---|---|---|
| | | 16 | 17 | 18 | 19 | 20 | 21 | 22 | 23 | 24 | 25 | 26 | 27 | 28 | 29 |
| antigen amount of administration (μg HA/dose) | | 0.3 | 0.1 | 0.033 | 0.3 | 0.1 | 0.033 | 0.3 | 0.1 | 0.033 | 0.3 | 0.3 | 0.3 | 0.3 | none (saline) |
| administration frequency | | | 3 | | | 2 | | | 1 | | 4 | 3 | 2 | 1 | 1 |
| administration route | | trans-nasal | trans-nasal | trans-nasal | trans-nasal | trans-nasal | trans-nasal | trans-nasal | trans-nasal | trans-nasal | intra-muscular | intra-muscular | intra-muscular | intra-muscular | trans-nasal |
| adjuvant (Ampligen), CVP addition | | none | none | none | none | none | none | none | none | none | none | none | none | none | none |
| animal No. | 1 | 80 | 80 | 20 | 40 | 80 | 160 | 20 | 10 | 20 | 320 | 640 | 80 | 80 | 20 |
| | 2 | 640 | 160 | 40 | 80 | 80 | 40 | 20 | 20 | 20 | 640 | 320 | 160 | 20 | 20 |
| | 3 | 640 | 20 | 40 | 160 | 40 | 40 | 10 | 20 | 20 | 640 | 320 | 640 | 10 | 20 |
| | 4 | 320 | 80 | 40 | 320 | 40 | 10 | 20 | 20 | 20 | 640 | 640 | 160 | 20 | 10 |
| | 5 | 160 | 40 | 40 | 320 | 40 | 40 | 20 | 20 | 20 | 160 | 640 | 160 | 20 | 5 |
| | 6 | 80 | 40 | 320 | 160 | 40 | 10 | 20 | 20 | 20 | 320 | 640 | 160 | 20 | 5 |
| | 7 | 640 | 20 | 80 | 20 | 20 | 40 | 20 | 20 | 40 | 640 | 640 | 160 | 40 | 10 |
| | 8 | 160 | 320 | 20 | 160 | 20 | 10 | 20 | 20 | 10 | 320 | 2560 | 160 | 20 | 10 |
| | 9 | 160 | 160 | 40 | 320 | 40 | 20 | 10 | 10 | 10 | 2560 | 320 | 640 | 40 | 10 |
| | 10 | 640 | | 40 | 160 | 40 | 20 | 20 | 20 | 5 | 2560 | 640 | 1280 | 20 | 10 |
| average antibody titer (GMT) | | 259.9 | 68.6 | 46.7 | 130.0 | 40.0 | 26.4 | 17.4 | 17.4 | 16.2 | 597.1 | 597.1 | 242.5 | 24.6 | 10.7 |
| variance | | 256.3 | 97.7 | 94.9 | 113.2 | 20.7 | 44.6 | 4.2 | 4.2 | 9.4 | 902.7 | 658.4 | 383.2 | 20.2 | 5.9 |

TABLE 17

New type Influ A/Indo Ampligen.CVP addition vaccine consideration of mouse dose.administration frequency; A/Qinghai strain serum NT test (2009 Nov. 6/9)

| | | group | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| antigen amount of administration (μg HA/dose) | | 0.3 | 0.1 | 0.033 | 0.3 | 0.1 | 0.033 | 0.3 | 0.1 | 0.033 | 0.3 | 0.1 | 0.033 | 0.3 | 0.1 | 0.033 |
| administration frequency | | | 4 | | | 3 | | | 2 | | | 1 | | | 4 | |
| administration route | | trans-nasal | trans-nasal | trans-nasal | trans-nasal | trans-nasal | trans-nasal | trans-nasal | trans-nasal | trans-nasal | trans-nasal | trans-nasal | trans-nasal | trans-nasal | trans-nasal | trans-nasal |
| adjuvant (Ampligen), CVP addition | | yes | yes | yes | yes | yes | yes | yes | yes | yes | yes | yes | yes | none | none | none |
| animal | 1 | 160 | 40 | 5 | 80 | 20 | | 5 | 40 | 40 | 20 | 20 | 160 | 80 | 160 | 20 |

TABLE 17-continued

New type Influ A/Indo Ampligen.CVP addition vaccine consideration of mouse dose.administration frequency; A/Qinghai strain serum NT test (2009 Nov. 6/9)

| | | | | | | | | | | | | | | | | |
|---|---|---|---|---|---|---|---|---|---|---|---|---|---|---|---|---|
| No. | 2 | 40 | 160 | 10 | 320 | 160 | 80 | 20 | 40 | 20 | 20 | 40 | 80 | 20 | 5 | 40 |
| | 3 | 320 | 20 | 10 | 320 | 20 | 40 | 80 | 40 | 20 | 20 | 20 | 80 | 20 | 20 | 40 |
| | 4 | 1280 | 10 | 20 | 40 | 10 | 10 | 5 | 160 | 40 | 20 | 160 | 40 | 40 | 320 | 20 |
| | 5 | 40 | 5 | 40 | 20 | 40 | 20 | 40 | 20 | 40 | 20 | 40 | 20 | 40 | 80 | 20 |
| | 6 | 20 | 320 | 10 | 160 | 40 | 40 | 80 | 80 | 40 | 40 | 40 | 10 | 40 | 160 | 40 |
| | 7 | 20 | 20 | 10 | 160 | 160 | 5 | 80 | 160 | 40 | 40 | 40 | 10 | 640 | 40 | 5 |
| | 8 | 640 | 10 | 20 | 80 | 20 | 80 | 80 | 80 | 40 | 40 | 160 | 5 | 80 | 80 | 20 |
| | 9 | 40 | | 20 | 160 | 80 | 20 | 160 | 80 | 40 | 20 | 20 | 5 | 80 | 80 | 10 |
| | 10 | 80 | | 80 | 160 | | | | | 40 | 20 | 80 | 20 | 40 | 40 | 40 |
| average antibody titer (GMT) | | 98.5 | 28.3 | 16.2 | 113.1 | 36.7 | 25.9 | 37.0 | 63.5 | 34.8 | 24.6 | 45.9 | 23.0 | 56.6 | 60.6 | 21.4 |
| variance | | 407.0 | 112.0 | 22.5 | 103.8 | 59.7 | 29.4 | 49.5 | 51.4 | 8.4 | 9.7 | 54.5 | 50.1 | 188.4 | 93.9 | 13.4 |

| | | group | | | | | | | | | | | | | |
|---|---|---|---|---|---|---|---|---|---|---|---|---|---|---|---|
| | | 16 | 17 | 18 | 19 | 20 | 21 | 22 | 23 | 24 | 25 | 26 | 27 | 28 | 29 |
| antigen amount of administration (μg HA/dose) | | 0.3 | 0.1 | 0.033 | 0.3 | 0.1 | 0.033 | 0.3 | 0.1 | 0.033 | 0.3 | 0.3 | 0.3 | 0.3 | none (saline) |
| administration frequency | | | 3 | | | 2 | | | 1 | | 4 | 3 | 2 | 1 | 1 |
| administration route | | trans-nasal | trans-nasal | trans-nasal | trans-nasal | trans-nasal | trans-nasal | trans-nasal | trans-nasal | trans-nasal | intra-mus-cular | intra-muscular | intra-mus-cular | intra-muscular | trans-nasal |
| adjuvant (Ampligen), CVP addition | | none | none | none | none | none | none | none | none | none | none | none | none | none | none |
| animal No. | 1 | 40 | 10 | 10 | 10 | 40 | 40 | 10 | 20 | 10 | 80 | 80 | 40 | 80 | 20 |
| | 2 | 20 | 40 | 20 | 40 | 40 | 20 | 10 | 20 | 10 | 160 | 40 | 80 | 40 | 20 |
| | 3 | 80 | 10 | 5 | 20 | 20 | 10 | 10 | 20 | 20 | 320 | 40 | 80 | 40 | 10 |
| | 4 | 40 | 80 | 20 | 40 | 20 | 20 | 20 | 20 | 20 | 160 | 640 | 40 | 5 | 5 |
| | 5 | 80 | 40 | 40 | 40 | 20 | 40 | 20 | 20 | 20 | 40 | 80 | 80 | 40 | 5 |
| | 6 | 20 | 20 | 5 | 40 | 20 | 20 | 20 | 20 | 20 | 80 | 80 | 160 | 40 | 5 |
| | 7 | 40 | 20 | 20 | 40 | 20 | 20 | 20 | 20 | 20 | 320 | 40 | 80 | 40 | 10 |
| | 8 | 80 | 80 | 20 | 20 | 10 | 5 | 20 | 20 | 40 | 160 | 160 | 40 | 5 | 20 |
| | 9 | 40 | 20 | 10 | 80 | 20 | 10 | 10 | 10 | 10 | 320 | 80 | 160 | 40 | 10 |
| | 10 | 160 | | 20 | 80 | 20 | 10 | 20 | 20 | 5 | 40 | 640 | 160 | 20 | 10 |
| average antibody titer (GMT) | | 49.2 | 27.2 | 14.1 | 34.8 | 21.4 | 16.2 | 15.2 | 18.7 | 15.2 | 130.0 | 105.6 | 80.0 | 26.4 | 10.0 |
| variance | | 42.2 | 27.4 | 10.3 | 23.3 | 9.5 | 12.1 | 5.2 | 3.2 | 9.8 | 114.4 | 240.8 | 50.1 | 21.6 | 6.3 |

TABLE 18

New type Influ A/Anhui Ampligen.CVP addition vaccine consideration of mouse dose.administration frequency; Serum NT test (2009 Jul. 27, Aug. 3)

| | | group | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| antigen amount of administration (μg HA/dose) | | 0.3 | 0.1 | 0.033 | 0.3 | 0.1 | 0.033 | 0.3 | 0.1 | 0.033 | 0.3 | 0.1 | 0.033 | 0.3 | 0.1 | 0.033 |
| administration frequency | | | 4 | | | 3 | | | 2 | | | 1 | | | 4 | |
| administration route | | trans-nasal | trans-nasal | trans-nasal | trans-nasal | trans-nasal | trans-nasal | trans-nasal | trans-nasal | trans-nasal | trans-nasal | trans-nasal | trans-nasal | trans-nasal | trans-nasal | trans-nasal |
| adjuvant (Ampligen), CVP addition | | yes | yes | yes | yes | yes | yes | yes | yes | yes | yes | yes | yes | none | none | none |
| animal No. | 1 | 640 | 160 | 40 | 80 | 320 | 20 | 640 | 160 | 80 | 20 | 80 | 20 | 10 | 20 | 160 |
| | 2 | 80 | 320 | 40 | 320 | 320 | 80 | 80 | 40 | 20 | 40 | 80 | 20 | 80 | 20 | 10 |
| | 3 | 1280 | 80 | 320 | 320 | 80 | 640 | 80 | 80 | 80 | 40 | 20 | 20 | 20 | 80 | 40 |
| | 4 | 160 | 320 | 80 | 320 | 80 | 40 | 640 | 40 | 40 | 40 | 20 | 40 | 20 | 160 | 20 |
| | 5 | 640 | 80 | 20 | 640 | 320 | 40 | 80 | 80 | 40 | 20 | 20 | 20 | 80 | 20 | 40 |
| | 6 | 320 | 640 | 10 | 640 | 320 | 20 | 80 | 80 | 40 | 40 | 20 | 10 | 80 | 80 | 20 |
| | 7 | 160 | 320 | 80 | 320 | 80 | 40 | 160 | 640 | 20 | 20 | 5 | 20 | 40 | 40 | 10 |
| | 8 | 160 | 10 | 640 | 80 | 320 | 80 | 640 | 160 | 640 | 80 | 20 | 5 | 40 | 10 | 10 |

TABLE 18-continued

New type Influ A/Anhui Ampligen.CVP addition vaccine consideration of mouse dose.administration frequency; Serum NT test (2009 Jul. 27, Aug. 3)

| | | | | | | | | | | | | | | | |
|---|---|---|---|---|---|---|---|---|---|---|---|---|---|---|---|
| | 9 | 640 | | 10 | 160 | 40 | 80 | 640 | 40 | 160 | 20 | 10 | 5 | 320 | 40 | 5 |
| | 10 | 20 | | 640 | 80 | | | | | 160 | 20 | 40 | 20 | 160 | 10 | 20 |
| average antibody titer (GMT) | | 242.5 | 146.7 | 69.6 | 226.3 | 160.0 | 58.8 | 217.7 | 93.3 | 69.6 | 30.3 | 23.0 | 15.2 | 52.8 | 32.5 | 20.0 |
| variance | | 390.5 | 203.4 | 254.9 | 210.1 | 132.3 | 198.2 | 287.8 | 190.8 | 187.2 | 19.0 | 27.1 | 10.1 | 93.7 | 47.1 | 46.1 |

| | | group | | | | | | | | | | | | | |
|---|---|---|---|---|---|---|---|---|---|---|---|---|---|---|---|
| | | 16 | 17 | 18 | 19 | 20 | 21 | 22 | 23 | 24 | 25 | 26 | 27 | 28 | 29 |
| antigen amount of administration (μg HA/dose) | | 0.3 | 0.1 | 0.033 | 0.3 | 0.1 | 0.033 | 0.3 | 0.1 | 0.033 | 0.3 | 0.3 | 0.3 | 0.3 | none (saline) |
| administration frequency | | | 3 | | | 2 | | | 1 | | 4 | 3 | 2 | 1 | 1 |
| administration route | | trans-nasal | trans-nasal | trans-nasal | trans-nasal | trans-nasal | trans-nasal | trans-nasal | trans-nasal | trans-nasal | intra-mus-cular | intra-muscular | intra-mus-cular | intra-muscular | trans-nasal |
| adjuvant (Ampligen), CVP addition | | none | none | none | none | none | none | none | none | none | none | none | none | none | none |
| animal No. | 1 | 160 | 20 | 40 | 20 | 20 | 40 | 20 | 20 | 20 | 320 | 20 | 80 | 20 | 20 |
| | 2 | 40 | 160 | 40 | 20 | 10 | 20 | 20 | 20 | 20 | 320 | 40 | 80 | 20 | 20 |
| | 3 | 80 | 20 | 40 | 40 | 20 | 80 | 20 | 20 | 20 | 320 | 160 | 40 | 20 | 20 |
| | 4 | 160 | 40 | 40 | 40 | 10 | 20 | 20 | 20 | 20 | 320 | 640 | 160 | 5 | 10 |
| | 5 | 80 | 40 | 40 | 80 | 20 | 20 | 20 | 20 | 20 | 80 | 160 | 80 | 20 | 5 |
| | 6 | 80 | 40 | 20 | 40 | 20 | 10 | 10 | 20 | 20 | 160 | 80 | 40 | 20 | 5 |
| | 7 | 40 | 40 | 40 | 20 | 20 | 10 | 20 | 20 | 20 | 160 | 1280 | 40 | 20 | 10 |
| | 8 | 160 | 160 | 40 | 40 | 10 | 10 | 20 | 20 | 20 | 320 | 160 | 40 | 5 | 20 |
| | 9 | 20 | 40 | 40 | 80 | 20 | 10 | 20 | 10 | 10 | 160 | 640 | 160 | 20 | 20 |
| | 10 | 80 | | 40 | 40 | 20 | 20 | 20 | 20 | 5 | 640 | 640 | 20 | 20 | 20 |
| average antibody titer (GMT) | | 74.6 | 46.7 | 37.0 | 37.3 | 16.2 | 18.7 | 18.7 | 18.7 | 16.2 | 242.5 | 197.0 | 60.6 | 15.2 | 13.2 |
| variance | | 52.7 | 56.1 | 6.7 | 22.0 | 4.8 | 21.7 | 3.2 | 3.2 | 5.4 | 156.6 | 407.3 | 49.9 | 6.3 | 6.7 |

TABLE 19

New type Influ A/Indo Ampligen.CVP addition vaccine consideration of mouse dose.administration frequency; Serum NT test (2009 Aug. 24, Aug. 27) cross-reaction (A/VN)

| | | group | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| antigen amount of administration (μg HA/dose) | | 0.3 | 0.1 | 0.033 | 0.3 | 0.1 | 0.033 | 0.3 | 0.1 | 0.033 | 0.3 | 0.1 | 0.033 | 0.3 | 0.1 | 0.033 |
| administration frequency | | | 4 | | | 3 | | | 2 | | | 1 | | | 4 | |
| administration route | | trans-nasal | trans-nasal | trans-nasal | trans-nasal | trans-nasal | trans-nasal | trans-nasal | trans-nasal | trans-nasal | trans-nasal | trans-nasal | trans-nasal | trans-nasal | trans-nasal | trans-nasal |
| adjuvant (Ampligen), CVP addition | | yes | yes | yes | yes | yes | yes | yes | yes | yes | yes | yes | yes | none | none | none |
| animal No. | 1 | 40 | 20 | 10 | 40 | 160 | 40 | 5 | 40 | 40 | 80 | 80 | 40 | 10 | 40 | 10 |
| | 2 | 20 | 40 | 40 | 80 | 20 | 80 | 10 | 80 | 20 | 80 | 80 | 40 | 40 | 5 | 20 |
| | 3 | 40 | 40 | 10 | 40 | 40 | 160 | 20 | 80 | 20 | 80 | 40 | 20 | 40 | 20 | 20 |
| | 4 | 160 | 40 | 80 | 40 | 10 | 40 | 10 | 40 | 40 | 80 | 40 | 40 | 10 | 80 | 10 |
| | 5 | 80 | 20 | 20 | 40 | 80 | 40 | 40 | 10 | 40 | 80 | 40 | 40 | 10 | 20 | 20 |
| | 6 | 10 | 80 | 10 | 20 | 40 | 20 | 20 | 40 | 40 | 80 | 20 | 10 | 10 | 20 | 20 |
| | 7 | 20 | 10 | 10 | 40 | 40 | 80 | 40 | 40 | 40 | 80 | 10 | 40 | 10 | 20 | 5 |
| | 8 | 40 | 10 | 20 | 80 | 40 | 40 | 10 | 40 | 40 | 80 | 40 | 5 | 20 | 20 | 10 |
| | 9 | 40 | | 20 | 40 | 80 | 20 | 80 | 40 | 40 | 80 | 40 | 5 | 20 | 20 | 5 |
| | 10 | 20 | | 80 | 80 | | | | | 80 | 80 | 40 | 40 | 40 | 20 | 20 |
| average antibody titer (GMT) | | 34.8 | 25.9 | 21.4 | 45.9 | 43.2 | 46.7 | 18.5 | 40.0 | 37.3 | 80.0 | 37.3 | 21.4 | 17.4 | 21.4 | 12.3 |
| variance | | 44.2 | 23.1 | 27.9 | 21.6 | 45.3 | 44.1 | 24.0 | 21.9 | 16.3 | 0.0 | 22.1 | 16.0 | 13.7 | 20.6 | 6.6 |

TABLE 19-continued

New type Influ A/Indo Ampligen.CVP addition vaccine consideration of mouse dose.administration frequency; Serum NT test (2009 Aug. 24, Aug. 27) cross-reaction (A/VN)

| | | group | | | | | | | | | | | | | |
|---|---|---|---|---|---|---|---|---|---|---|---|---|---|---|---|
| | | 16 | 17 | 18 | 19 | 20 | 21 | 22 | 23 | 24 | 25 | 26 | 27 | 28 | 29 |
| antigen amount of administration (μg HA/dose) | | 0.3 | 0.1 | 0.033 | 0.3 | 0.1 | 0.033 | 0.3 | 0.1 | 0.033 | 0.3 | 0.3 | 0.3 | 0.3 | none saline) |
| administration frequency | | | 3 | | | 2 | | | 1 | | 4 | 3 | 2 | 1 | 1 |
| administration route | | trans-nasal | trans-nasal | trans-nasal | trans-nasal | trans-nasal | trans-nasal | trans-nasal | trans-nasal | trans-nasal | intra-mus-cular | intra-muscular | intra-mus-cular | intra-muscular | trans-nasal |
| adjuvant (Ampligen), CVP addition | | none | none | none | none | none | none | none | none | none | none | none | none | none | none |
| animal No. | 1 | 40 | 40 | 40 | 20 | 40 | 40 | 40 | 20 | 40 | 80 | 20 | 80 | 80 | 40 |
| | 2 | 40 | 40 | 40 | 40 | 20 | 40 | 20 | 40 | 40 | 20 | 40 | 80 | 40 | 80 |
| | 3 | 40 | 20 | 40 | 20 | 40 | 20 | 40 | 40 | 40 | 80 | 40 | 80 | 40 | 40 |
| | 4 | 20 | 40 | 40 | 40 | 5 | 40 | 40 | 80 | 40 | 80 | 160 | 40 | 5 | 10 |
| | 5 | 80 | 40 | 40 | 40 | 40 | 40 | 20 | 20 | 40 | 20 | 80 | 40 | 40 | 5 |
| | 6 | 80 | 20 | 40 | 20 | 40 | 20 | 20 | 40 | 40 | 40 | 80 | 40 | 40 | 5 |
| | 7 | 40 | 40 | 40 | 20 | 40 | 20 | 40 | 20 | 40 | 40 | 40 | 40 | 40 | 20 |
| | 8 | 20 | 20 | 40 | 20 | 10 | 20 | 40 | 40 | 40 | 160 | 80 | 40 | 10 | 40 |
| | 9 | 20 | 40 | 40 | 40 | 40 | 20 | 20 | 20 | 20 | 20 | 80 | 40 | 80 | 20 |
| | 10 | 80 | | 40 | 5 | 40 | 40 | 40 | 40 | 10 | 20 | 80 | 40 | 40 | 20 |
| average antibody titer (GMT) | | 40.0 | 31.7 | 40.0 | 23.0 | 26.4 | 28.3 | 30.3 | 32.5 | 32.5 | 42.9 | 60.6 | 40.0 | 32.5 | 20.0 |
| variance | | 25.0 | 10.0 | 0.0 | 12.5 | 14.2 | 10.5 | 10.3 | 18.4 | 10.8 | 45.0 | 39.2 | 19.3 | 24.3 | 22.9 |

EXAMPLE 3

Administration of Transnasal Administration-Type Influenza Vaccine (H5N1 Type) and Immune Response Evaluation Test Using Cynomolgus Monkeys (*Macaca fascicularis*)

Based on the relationship between the administration dose, use and immune response obtained by the experiments using mice in Example 2, administration tests were performed using Cynomolgus monkeys (*Macaca fascicularis*) as an animal close to human, and the dosage form and composition optimal as a transnasal administration-type vaccine were searched and the usefulness from the aspect of infection defense was investigated.

To be precise, (1) search of optimal dosage form/composition by comparison of immune responses after administration of transnasal administration-type vaccine candidates, and (2) evaluation of practicality from the ability to defend against infection by measurement of serum and mucous membrane antibody titers after vaccine inoculation were performed.

The search was performed by immuno-chemical test of serum (influenza HI antibody titer, IgG-ELISA antibody titer and neutralizing antibody titer) and immuno-chemical test of nasal swab (influenza specific IgA-ELISA antibody titer).

(Test Method)

1. Influenza vaccine stock solution:

Influenza vaccine (H5N1 strain) stock solution (lot No., FPBMQI0813, protein concentration: 816 μg/mL, HA content 324 μg HA/mL, origin of virus strain: A/Bar-headed Goose/Qinghai/1A/2005 (H5N1))

2. Origin of virus strain and inactivated vaccine antigen to be used for test (for specific antibody titer measurement)

A/Bar-headed Goose/Qinghai/1A/2005 (H5N1) strain: attenuated strain (clade 2.2) of A/Qinghai/1A/2005 (H5N1)

(for cross-reactive antibody titer measurement)

A/Indo/5/2005 (H5N1)/PR8-IBCDC-RG2 strain: attenuated strain (clade 2.1) of A/Indonesia/5/2005 (H5N1)

A/Anhui/01/2005 (H5N1)/PR8-IBCDC-RG5 strain: attenuated strain (clade 2.3) of A/Anhui/01/2005 (H5N1)

NIBRG-14 strain: attenuated strain (clade 1) of A/Vietnam/1194/2004 (H5N1)

3. Adjuvant and additive to be used for test

Ampligen: manufactured by Hemispherx, (containing 10.61 mg/mL of Ampligen)

carboxyvinyl polymer (CVP): manufactured by Toko Yakuhin Kogyo Kabushiki Kaisya, lot; INF-619 (containing 1.1% CVP, 2.4% L-arginine and 2% glycerol)

poly L-arginine: manufactured by SIGMA, catalog No. P-3892, lot; 107K5103 (MW>70,000)

4. Test method

Figure 4:
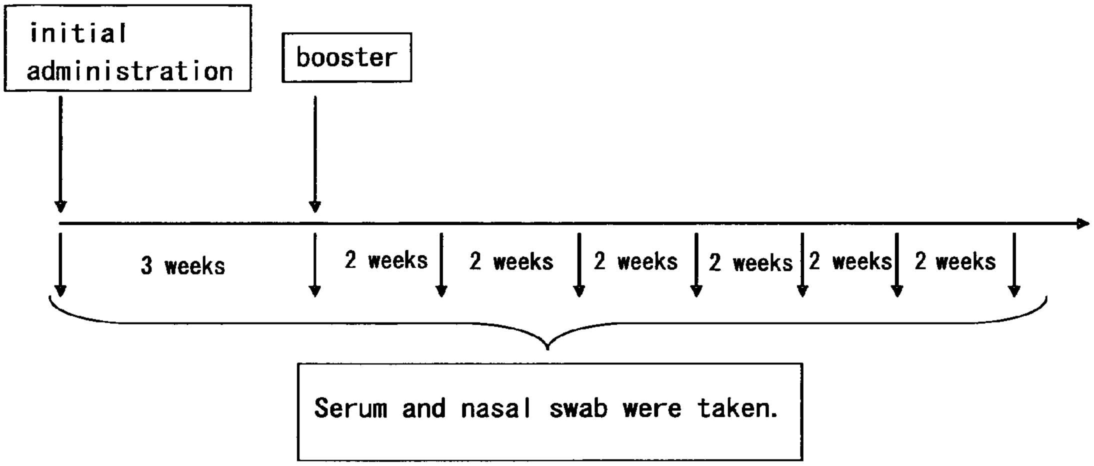
FIG. 4 is a flow chart of monkey immunity test in Example 3.

FIG. 4 shows outline of test flows.

TABLE 20

Test group constitution:

| group | vaccine HA antigen (μg/dose) | Ampligen (μg/dose) | Poly L-Arg (μg/dose) | CVP addition | head | note |
|---|---|---|---|---|---|---|
| 1 | 30 | | | — | 4 | vaccine alone |
| 2 | 30 | 600 | | ○ | 4 | trial vaccine |
| 3 | 30 | | 1500 | ○ | 4 | Poly L-Arg |
| 4 | — | | | — | 1 | control group |

Anesthesized Cynomolgus monkeys (*Macaca fascicularis*) was transnasally administered with a vaccine containing A/Bar-headed Goose/Qinghai/1A/2005 (H5N1) strain virus antigen or saline at 3 weeks intervals, using a transnasal administration device with trial actuator (test actuator: manufactured by Toko Yakuhin Kogyo Kabushiki Kaisya, Spray Pump; Apta Pharma, VP-7 type, spraying use) six times by 150 μl (50 μl×3) to each nasal cavity (total 300 μl), and samples (nasal swab and serum) were taken at the time of each administration, and every 2 weeks from the booster up to 12 weeks from the booster. Furthermore, where necessary, blood samples nasal swab were taken every 2 weeks thereafter.

Animal and Vaccine:

animal: Cynomolgus monkeys (*Macaca fascicularis*) (male 17 cynomolgus monkeys, 46-58 months of age when test was started, body weight 2.8-3.5 kg in November 2009), group 1-group 4: 4 cynomolgus monkeys/group, group 5 (negative control): cynomolgus monkey/group trial vaccine for test and adjuvant dose:

(1) non-addition vaccine group: [30 μg HA]/dose (2) Ampligen+CVP addition vaccine group: [30 μg HA+600 μg Ampligen+0.55% CVP]/dose (3) Poly L-arginine+CVP addition vaccine group: [30 μg HA+0.5% Poly L-arginine+0.55% CVP]/dose (4) negative control group: saline vaccine administration volume: 150 μl for each nasal cavity, total 300 μl 5. Measurement items of each sample nasal swab: specific IgA-ELISA antibody titer and IgA concentration The nasal swab was measured for the total IgA concentration and the specific IgA-ELISA antibody titer calculated in the same manner as in Example 2 was amended to be the numerical value per total IgA concentration of 1 μg/mL.

serum: specific IgG-ELISA antibody titer, specific, cross-reactive HI (hemagglutination inhibition) antibody titer, specific/cross-reactive neutralizing antibody titer Among the above-mentioned measurement items, the outline of the measurement method of the ELISA antibody titer was as described below.

Vaccine antigen (diluted with 100 mM carbonate buffer (pH 9.6) to protein concentration of 1 μg/mL) was solid phased (4° C., overnight) on a 96-well ELISA plate at 100 μL/well, and washed 3 times with PBS containing 0.1% Tween 20. A sample diluted 2-fold series or negative control was added at 100 μL/well. Then, the plate was incubated at 37° C. for 1 hr, and washed 3 times with PBS containing 0.1% Tween 20. An antibody for detection (alkaliphosphatase-labeled anti-monkey IgG or biotin-labeled anti-monkey IgA) was added at 100 μL/well. The plate was incubated at 37° C. for 1 hr, and washed 3 times with PBS containing 0.1% Tween 20. The substrate solution (4-NPP or TMB) was added at 100 μL/well and the mixture was shaded and incubated at room temperature for 30 min.

A stop solution (2M $H_2SO_4$ solution for 4-NPP or 650 nm stop solution for TMB) was added, and the absorbance (405 nm or 655 nm) was measured.

The maximum dilution rate that affords an absorbance of sample exceeding the average absorbance of negative control+2SD was taken as the antibody titer of the sample. For specific antibody titer, the same strain as the administration vaccine antigen was used and, for cross-reactive antibody titer, vaccine antigen of a different strain was used. In the following, HI antibody titer and neutralizing antibody titer were measured in the same manner.

specific HI (hemagglutination inhibition) antibody titer and cross-reactive HI antibody titer: They were measured in the same manner as in Example 2.

specific neutralizing antibody titer and cross-reactive neutralizing antibody titer: They were measured in the same manner as in Example 2.

(Results)

Figure 5:
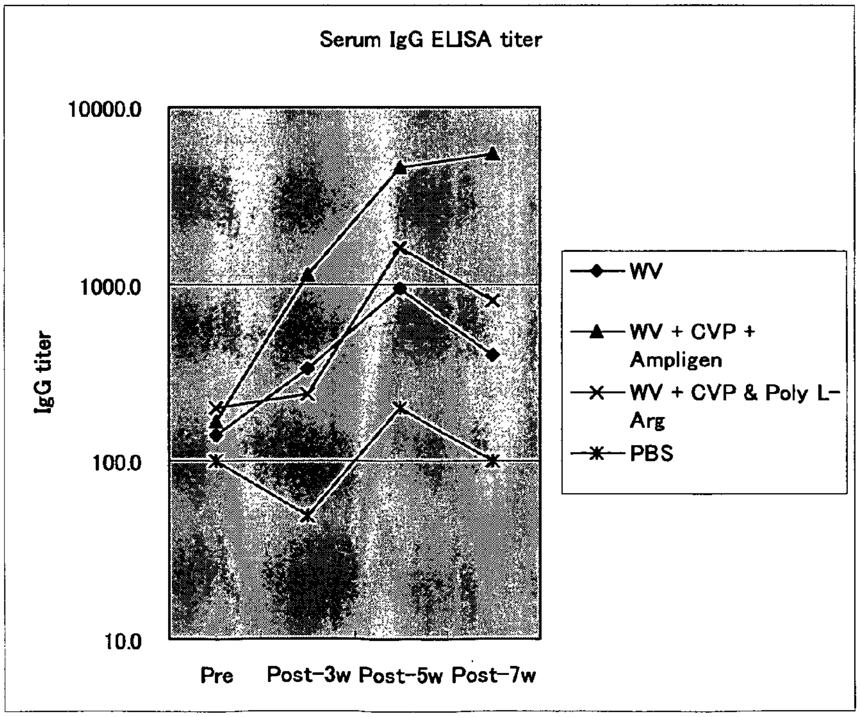
FIG. 5 shows the results of Serum IgG ELISA in Example 3.
Figure 6:
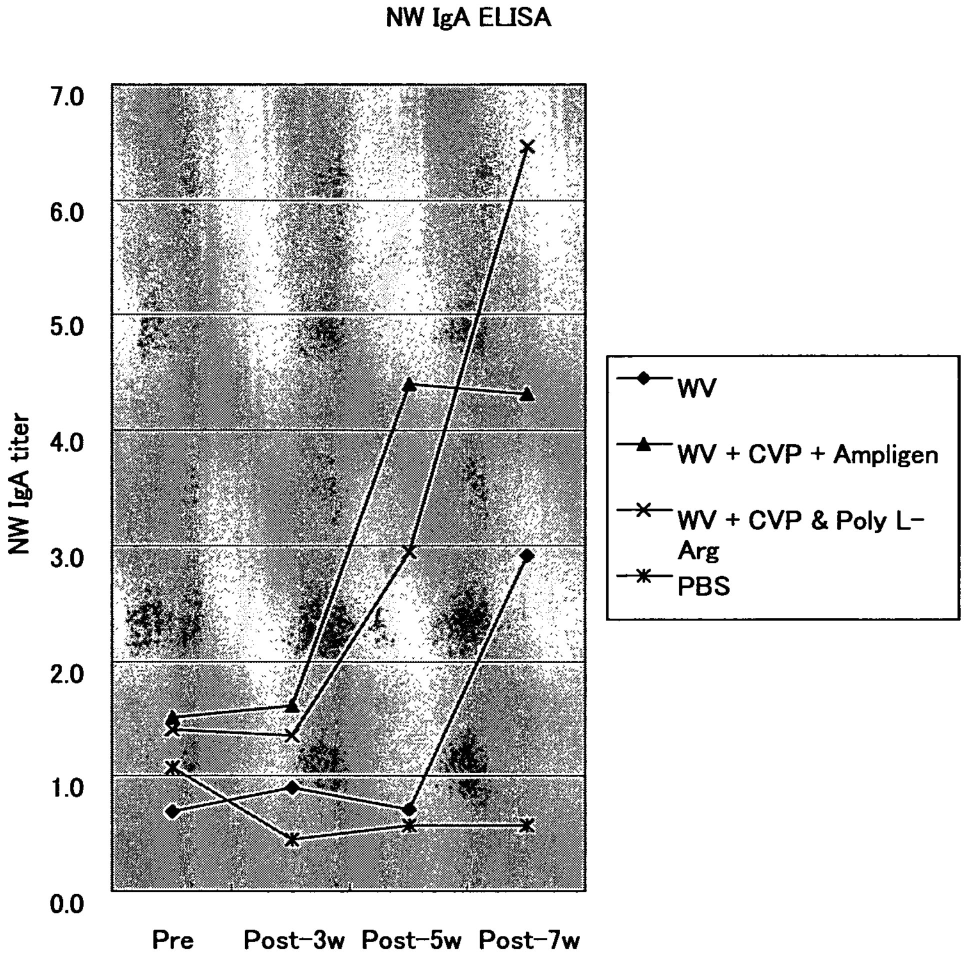
FIG. 6 shows the results of nasal swab IgA ELISA in Example 3.
Figure 7:
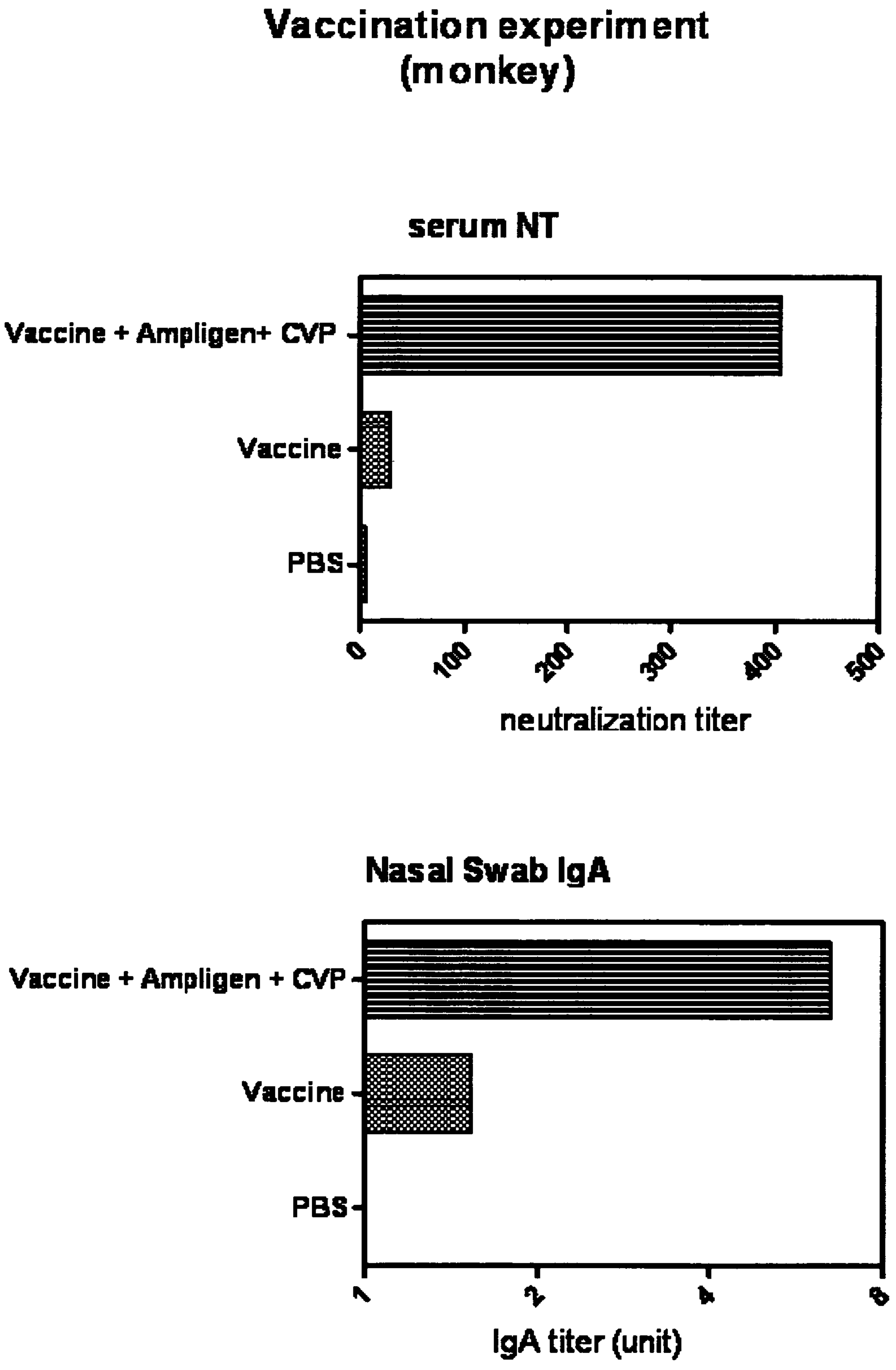
FIG. 7 shows a summary of the vaccine administration test in Example 3.

The results are shown in Tables 21-30 and FIGS. 5-7.

It was confirmed that transnasal spray administration of a vaccine containing Ampligen and CVP to monkey induces specific IgA production in the mucous membrane, and derivation of specific neutralizing antibody in the serum. Since these effects were insufficient with an additive-free vaccine, the usefulness of addition of Ampligen and CVP was confirmed.

TABLE 21

Administration of transnasal administration-type influenza vaccine (H5N1-type) and immune response evaluation test using Cynomolgus monkeys (*Macaca fascicularis*); Vaccine composition

| group | vaccine HA antigen (mL) [324 μg HA/mL] | Ampligen (mL) [10.61 mg/mL] | Poly L-Arg (mL) [100 mg/mL] | CVP addition (mL) | M/75 PBS (pH 7.2) (mL) | Note | dose (μL) |
|---|---|---|---|---|---|---|---|
| 1 | 3.087 (30 μg/dose) | — | — | — | 6.913 | 10 mL min | 300 |
| 2 | 3.087 30 μg/dose) | 1.885 (600 μg/dose) | — | 5.0 (yes) | 0.028 | 10 mL min | 300 |
| 3 | — | — | 0.750 (1.5 mg/dose) | — | 4.250 | 5 mL min | 100 |
| | 3.704 (30 μg/dose) | — | — | 4 | 0.296 | 8 mL min | 200 |
| 4 | | — | — | — | 10.000 | 10 mL min | 300 |

Influenza vaccine stock solution to be used for test influenza vaccine (H5N1 strain) stock solution: lot No.; FPBMQI0813 (protein concentration: 816 μg/mL, HA content 324 μg HA/mL)
origin virus strain: A/Bar-headed Goose/Qinghai/1A/2005 (H5N1) adjuvant and additive to be used for test Ampligen (manufactured by Hemispherx): containing 10.61 mg/mL of Ampligen carboxyvinyl polymer (manufactured by Toko Yakuhin Kogyo Kabushiki Kaisya): lot; INF-619 (containing 1.1% CVP (carboxyvinyl polymer), 2.4% L-arginine and 2% glycerol)
poly L-arginine (manufactured by SIGMA, catalog No. P-3892): lot; used after dissolving 107K5103 (MW > 70,000) in 100 mg/mL

TABLE 22

Administration of transnasal administration-type influenza vaccine (H5N1-type) and immune response evaluation test (HI) using Cynomolgus monkeys (*Macaca fascicularis*); before administration (blood samples were collected on 2010 Jan. 28/measured on 2010 Feb. 2)

| group | | 1 | 2 | 3 | 4 |
|---|---|---|---|---|---|
| vaccine HA antigen (μg/dose) | | 30 | 30 | 30 | — |
| Ampligen (μg/dose) | | | 600 | | |
| Poly L-Arg (μg/dose) | | | | 1500 | |
| CVP addition | | − | + | + | − |
| animal No. | 1 | 5 | 5 | 5 | 5 |
| | 2 | 5 | 5 | 5 | |

TABLE 22-continued

Administration of transnasal administration-type influenza vaccine (H5N1-type) and immune response evaluation test (HI) using Cynomolgus monkeys (*Macaca fascicularis*); before administration (blood samples were collected on 2010 Jan. 28/measured on 2010 Feb. 2)

| group | | 1 | 2 | 3 | 4 |
|---|---|---|---|---|---|
| | 3 | 5 | 5 | 5 | |
| | 4 | 5 | 5 | 5 | |
| average antibody titer (GMT) | | 5.0 | 5.0 | 5.0 | 5.0 |
| variance | | 0.0 | 0.0 | 0.0 | |
| seroconversion rate (antibody titer not less than 40, %) | | 0.0 | 0.0 | 0.0 | 0.0 |

TABLE 23

Administration of transnasal administration-type influenza vaccine (H5N1-type) and immune response evaluation test (HI) using Cynomolgus monkeys (*Macaca fascicularis*); after once administration (blood samples were collected on 2010 Feb. 18/measured on 2010 Feb. 23)

| group | | 1 | 2 | 3 | 4 |
|---|---|---|---|---|---|
| vaccine HA antigen (μg/dose) | | 30 | 30 | 30 | — |
| Ampligen (μg/dose) | | | 600 | | |
| Poly L-Arg (μg/dose) | | | | 1500 | |
| CVP addition | | − | + | + | − |
| animal No. | 1 | 20 | 5 | 5 | 5 |
| | 2 | 10 | 5 | 5 | |
| | 3 | 5 | 5 | 5 | |
| | 4 | 5 | 10 | 5 | |
| average antibody titer (GMT) | | 8.4 | 5.9 | 5.0 | 5.0 |
| variance | | 7.1 | 2.5 | 0.0 | |
| seroconversion rate (antibody titer not less than 40, %) | | 0.0 | 0.0 | 0.0 | 0.0 |

TABLE 24

Administration of transnasal administration-type influenza vaccine (H5N1-type) and immune response evaluation test (HI) using Cynomolgus monkeys (*Macaca fascicularis*); after twice administration (blood samples were collected on 2010 Mar. 4/measured on 2010 Mar. 9)

| group | | 1 | 2 | 3 | 4 |
|---|---|---|---|---|---|
| vaccine HA antigen (μg/dose) | | 30 | 30 | 30 | — |
| Ampligen (μg/dose) | | | 600 | | |
| Poly L-Arg (μg/dose) | | | | 1500 | |
| CVP addition | | − | + | + | − |
| animal No. | 1 | 5 | 5 | 5 | 5 |
| | 2 | 5 | 5 | 5 | |
| | 3 | 5 | 5 | 5 | |
| | 4 | 5 | 5 | 5 | |
| average antibody titer (GMT) | | 5.0 | 5.0 | 5.0 | 5.0 |
| variance | | 0.0 | 0.0 | 0.0 | |
| seroconversion rate (antibody titer not less than 40, %) | | 0.0 | 0.0 | 0.0 | 0.0 |

TABLE 25

Administration of transnasal administration-type influenza vaccine (H5N1-type) and immune response evaluation test (HI) using Cynomolgus monkeys (*Macaca fascicularis*); 2 weeks after twice administration (blood samples were collected on 2010 Mar. 18/measured on 2010 Mar. 24)

| group | | 1 | 2 | 3 | 4 |
|---|---|---|---|---|---|
| vaccine HA antigen (μg/dose) | | 30 | 30 | 30 | — |
| Ampligen (μg/dose) | | | 600 | | |
| Poly L-Arg (μg/dose) | | | | 1500 | |
| CVP addition | | − | + | + | − |
| animal No. | 1 | 5 | 5 | 5 | 5 |
| | 2 | 5 | 5 | 5 | |
| | 3 | 5 | 5 | 5 | |
| | 4 | 5 | 5 | 5 | |
| average antibody titer (GMT) | | 5.0 | 7.1 | 5.9 | 5.0 |
| variance | | 0.0 | 2.9 | 2.5 | |
| seroconversion rate (antibody titer not less than 40, %) | | 0.0 | 0.0 | 0.0 | 0.0 |

TABLE 26

Administration of transnasal administration-type influenza vaccine (H5N1-type) and immune response evaluation test (NT) using Cynomolgus monkeys (*Macaca fascicularis*); before administration (blood samples were collected on 2010 Jan. 28/measured on 2010 Feb. 2)

| group | | 1 | 2 | 3 | 4 |
|---|---|---|---|---|---|
| vaccine HA antigen (μg/dose) | | 30 | 30 | 30 | — |
| Ampligen (μg/dose) | | | 600 | | |
| Poly L-Arg (μg/dose) | | | | 1500 | |
| CVP addition | | − | + | + | − |
| animal No. | 1 | 5 | 10 | 5 | 5 |
| | 2 | 5 | 10 | 20 | |
| | 3 | 5 | 5 | 10 | |
| | 4 | 5 | 5 | 20 | |
| average antibody titer (GMT) | | 5.0 | 7.1 | 11.9 | 5.0 |
| variance | | 0.0 | 2.9 | 7.5 | |

TABLE 27

Administration of transnasal administration-type influenza vaccine (H5N1-type) and immune response evaluation test (NT) using Cynomolgus monkeys (*Macaca fascicularis*) after NT administration once (blood samples were 2010 Feb. 18/measured on 2010 Feb. 23)

| group | | 1 | 2 | 3 | 4 |
|---|---|---|---|---|---|
| vaccine HA antigen (μg/dose) | | 30 | 30 | 30 | — |
| Ampligen (μg/dose) | | | 600 | | |
| Poly L-Arg (μg/dose) | | | | 1500 | |
| CVP addition | | − | + | + | − |
| animal No. | 1 | 5 | 10 | 20 | 5 |
| | 2 | 10 | 20 | 5 | |
| | 3 | 20 | 20 | 10 | |
| | 4 | 5 | 160 | 140 | |
| average antibody titer (GMT) | | 8.4 | 28.3 | 19.3 | 5.0 |
| variance | | 7.1 | 71.8 | 64.5 | |

TABLE 28

Administration of transnasal administration-type influenza vaccine (H5N1-type) and immune response evaluation test (NT) using Cynomolgus monkeys (*Macaca fascicularis*) after NT administration twice (blood samples were collected on 2010 Mar. 4/measured on 2010 Mar. 9)

| group | | 1 | 2 | 3 | 4 |
|---|---|---|---|---|---|
| vaccine HA antigen (μg/dose) | | 30 | 30 | 30 | — |
| Ampligen (μg/dose) | | | 600 | | |
| Poly L-Arg (μg/dose) | | | | 1500 | |
| CVP addition | | − | + | + | − |
| animal No. | 1 | 20 | 20 | 80 | 5 |
| | 2 | 40 | 160 | 5 | |
| | 3 | 40 | 160 | 80 | |
| | 4 | 10 | 1280 | 40 | |
| average antibody titer (GMT) | | 23.8 | 160.0 | 33.6 | 5.0 |
| variance | | 15.0 | 587.1 | 36.1 | |

TABLE 29

Serum IgG ELISA titer after administration of transnasal administration-type influenza vaccine (H5N1-type) using *Macaca fascicularis*

| group | | 1 | 2 | 3 | 4 |
|---|---|---|---|---|---|
| antibody titer | Pre | 141.4 | 168.2 | 200.0 | 100.0 |
| | Post-3 w | 336.4 | 1131.4 | 237.8 | 50.0 |
| | Post-5 w | 951.4 | 4525.5 | 1600.0 | 200.0 |
| | Post-7 w | 400.0 | 5381.7 | 800.0 | 100.0 |

TABLE 30

Nasal swab IgA ELISA titer after administration of transnasaladministration-type influenza vaccine (H5N1-type) using Cynomolgus monkeys (*Macaca fascicularis*)

| group | | 1 | 2 | 3 | 4 |
|---|---|---|---|---|---|
| antibody titer | Pre | 0.7 | 1.5 | 1.4 | 1.1 |
| | Post-3 w | 0.9 | 1.6 | 1.3 | 0.5 |
| | Post-5 w | 0.7 | 4.4 | 2.9 | 0.6 |
| | Post-7 w | 2.9 | 4.3 | 6.5 | 0.6 |

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

All of the references cited herein, including patents, patent applications, and publications, are hereby incorporated in their entireties by reference.

This application is based on a provisional patent application No. 61/165,098 filed in USA (filing date: Mar. 31, 2009), the contents of which are incorporated, in full herein by this reference.

The invention claimed is:

1. A composition for nasal mucosal administration, comprising at least one influenza virus antigen, polyriboinosinic polyribocytidylic acid (poly (I:C)) or a derivative thereof and a carboxyvinyl polymer, wherein the weight ratio of the influenza virus antigen and the poly (I:C) or derivative thereof is 1:1-1:50, and wherein the concentration of the carboxyvinyl polymer in the composition is 0.1 to 2.0 wt %.

2. The composition of claim 1, wherein the influenza virus antigen is a subunit antigen or an inactivated antigen.

3. The composition of claim 2, wherein the influenza virus antigen comprises at least one subunit antigen selected from the group consisting of HA, NA, M1, M2, NP, PB1, PB2, PA and NS2 of influenza virus.

4. The composition of claim 2, wherein the influenza virus antigen comprises at least one subunit antigen selected from the group consisting of HA and NA.

5. The composition of claim 4, wherein the subunit antigen comprises the HA subunit antigen.

6. The composition of claim 2, wherein the inactivated antigen is a complete virus particle virion.

7. The composition of claim 1, wherein the concentration of the poly(I:C) in the composition is 0.1 to 10 mg/mL.

8. The composition of claim 1, wherein the influenza virus antigen is from a subtype selected from the group consisting of H2, H4-H16, and N1-N9.

9. The composition of claim 1, wherein the influenza virus antigen is of a virus strain selected from the group consisting of A/Hiroshima/52/2005(H3N2), A/Indo/5/2005(H5N1)/PR8-IBCDC-RG2, A/Anhui/01/2005(H5N1)/PR8-IBCDC-RG5, A/Bar-headed Goose/Qinghai/1A/2005 (H5N1) and NIBRG-14.

10. The composition of claim 1, wherein the influenza antigen comprises an HA antigen which is present at a concentration of 10 to 500 μg/mL in the composition.

11. The composition of claim 10, wherein the concentration of the HA antigen in the composition is 30 to 400 μg/mL.

12. The composition of claim 1, which is suitable for administration to mammals or birds.

13. The composition of claim 12, which is suitable for administration to humans.

14. The composition of claim 1, wherein the concentration of the carboxyvinyl polymer in the composition is 0.55% and the amount of the poly (I:C) or derivative thereof in the composition is 1 μg/dose.

15. A method of inducing an immune response against influenza virus in a subject, comprising administering at least once to the nasal mucosa of the subject a composition comprising an effective amount of an influenza virus antigen, poly (I:C) or a derivative thereof, and a carboxyvinyl polymer, wherein the weight ratio of the influenza virus antigen and the poly (I:C) or derivative thereof is 1:1-1:50, and wherein the concentration of the carboxyvinyl polymer in the composition is 0.1 to 2.0 wt %, thereby inducing an immune response against influenza virus in the subject.

16. The method of claim 15, wherein the influenza virus antigen is a subunit antigen or an inactivated antigen.

17. The method of claim 16, wherein the influenza virus antigen comprises at least one subunit antigen selected from the group consisting of HA, NA, M1, M2, NP, PB1, PB2, PA and NS2 of influenza virus.

18. The method of claim 16, wherein the influenza virus antigen comprises at least one subunit antigen selected from the group consisting of HA and NA.

19. The method of claim 18, wherein the subunit antigen comprises the HA subunit antigen.

20. The method of claim 16, wherein the inactivated antigen is a complete virus particle virion.

21. The method of claim 15, wherein the composition is administered at least twice.

22. The method of claim 21, wherein the composition is administered at an interval of at least 1 week.

23. The method of claim 15, wherein the antigen comprises an HA antigen which is present at a concentration of 10 to 500 μg/mL in the composition.

24. The method of claim 23, wherein the concentration of the HA antigen in the composition is 30 to 400 μg/mL.

25. The method of claim 15, wherein the subject is a mammal or a bird.

26. The method of claim 25, wherein the subject is a human.

27. The method of claim 15, wherein the concentration of the carboxyvinyl polymer in the composition is 0.55% and the amount of the poly (I:C) or derivative thereof in the composition is 1 μg/dose.

* * * * *